(12) United States Patent
Little et al.

(10) Patent No.: US 9,698,545 B2
(45) Date of Patent: Jul. 4, 2017

(54) MACHINE CASE WITH IMPROVED TERMINAL MODULE

(71) Applicant: FOXCONN INTERCONNECT TECHNOLOGY LIMITED, Grand Cayman (KY)

(72) Inventors: Terrance F. Little, Fullerton, CA (US); Chun-Yi Chang, New Taipei (TW)

(73) Assignee: FOXCONN INTERCONNECT TECHNOLOGY LIMITED, Grand Cayman (KY)

(*) Notice: Subject to any disclaimer, the term of this patent is extended or adjusted under 35 U.S.C. 154(b) by 0 days.

(21) Appl. No.: 14/942,978

(22) Filed: Nov. 16, 2015

(65) Prior Publication Data
US 2016/0141771 A1  May 19, 2016

Related U.S. Application Data

(60) Provisional application No. 62/085,478, filed on Nov. 28, 2014, provisional application No. 62/080,250, filed on Nov. 14, 2014, provisional application No. 62/203,865, filed on Aug. 11, 2015, provisional application No. 62/083,159, filed on Nov. 21, 2014.

(51) Int. Cl.
| | |
|---|---|
| H01R 12/00 | (2006.01) |
| H01R 13/73 | (2006.01) |
| H01R 13/405 | (2006.01) |
| G06F 1/16 | (2006.01) |

(52) U.S. Cl.
CPC .......... *H01R 13/73* (2013.01); *G06F 1/1632* (2013.01); *H01R 13/405* (2013.01); *A61B 2562/225* (2013.01); *H01R 2201/12* (2013.01)

(58) Field of Classification Search
CPC ... H01R 13/73; H01R 31/005; H01R 31/2453

USPC .......... 439/66, 577; 600/300, 301, 476, 595, 600/509, 549; 361/697
See application file for complete search history.

(56) References Cited

U.S. PATENT DOCUMENTS

| | | | |
|---|---|---|---|
| 5,289,824 A * | 3/1994 | Mills | A61B 5/0404 128/904 |
| 6,086,424 A * | 7/2000 | Chang | H01R 12/57 439/630 |
| 7,181,350 B2 * | 2/2007 | Oberding | H02J 7/0044 600/485 |
| 7,435,100 B2 * | 10/2008 | Chang | H01R 13/2435 439/66 |
| 7,654,868 B1 * | 2/2010 | Wang | G06K 7/0021 439/630 |
| 8,282,431 B1 * | 10/2012 | Zhang | H01R 12/714 439/591 |

(Continued)

*Primary Examiner* — Tulsidas C Patel
*Assistant Examiner* — Peter G Leigh
(74) *Attorney, Agent, or Firm* — Wei Te Chung; Ming Chieh Chang

(57) ABSTRACT

A machine case includes a sink-like main portion and opposite deck stations by two ends of said main portion, and a terminal module. Said terminal module includes an insulator defining opposite top and bottom surfaces and a set of contacts retained to the insulator via a first insert molding process and arranged along a transverse direction. Each of said contacts is stamped and bent from sheet metal and unitarily formed with an upper contacting section and a lower contacting section. One of said upper contacting section and said lower contacting section defines an exposed end for originally linking to a contact carrier. The insulator forms a set of recesses originally formed between the contacting sections of neighboring contacts during the first insert molding while successively filled with material by the corresponding deck station in which said terminal module is embedded.

20 Claims, 28 Drawing Sheets

(56) References Cited

U.S. PATENT DOCUMENTS

| | | | |
|---|---|---|---|
| 8,321,004 B2* | 11/2012 | Moon | A61B 5/0006 600/509 |
| 8,523,615 B2* | 9/2013 | Luo | H01R 12/7082 439/660 |
| 8,682,598 B2* | 3/2014 | Connolly | A61B 5/0002 702/32 |
| 8,688,188 B2* | 4/2014 | Heller | A61B 5/14532 600/345 |
| 8,915,850 B2* | 12/2014 | Heller | A61B 5/14532 204/403.01 |
| 9,439,574 B2* | 9/2016 | McCombie | A61B 5/02427 |
| 2011/0224498 A1* | 9/2011 | Banet | A61B 5/00 600/300 |
| 2011/0224508 A1* | 9/2011 | Moon | A61B 5/00 600/301 |
| 2012/0296174 A1 | 11/2012 | McCombie et al. | |
| 2014/0221797 A1* | 8/2014 | Bailey | A61B 5/0002 600/324 |
| 2015/0171648 A1* | 6/2015 | Williams | H01R 13/7175 320/107 |
| 2015/0346766 A1* | 12/2015 | Justice | G06F 1/163 361/679.03 |
| 2016/0141814 A1* | 5/2016 | Little | H01R 13/405 439/529 |
| 2016/0141819 A1* | 5/2016 | Chang | H01R 31/005 439/529 |

\* cited by examiner

330

MACHINE CASE WITH IMPROVED TERMINAL MODULE

This application claims the benefit of, and priorities to U.S. Provisional Patent Applications No. 62/080,250, filed Nov. 14, 2014; No. 62/083,159, filed Nov. 21, 2014; No. 62/085,478, filed Nov. 28, 2014; and No. 62/203,865, filed Aug. 11, 2015. The instant application relates to the copending application titled "ELECTRICAL CONNECTOR FOR USE WITH CRADLE" and "MACHINE CASE WITH IMPROVED ELECTRICAL CONNECTOR" having some commonly inventors, and the same applicant and the same assignee with the instant application.

BACKGROUND OF THE INVENTION

1. Field of the Invention

The invention relates to a machine case with terminal module for connecting a plurality of cables via a cradle.

2. Description of Related Art

Wearable medical technology is becoming a hot commodity, as these devices come to market; they have the potential to help both patients and clinicians monitor vital signs and symptoms. The wearable medical device usually comprises a cradle, a machine case attached to the cradle for housing processing module such as processor and associated electronics, and cables with plugs inserted into the cradle. During use, the machine case reversibly snaps into the cradle, upon mating of the cradle and the machine case, interface cavities are formed on the cradle for receiving the plugs of the cables leading to one or more peripheral devices such as sensors which collect data related to the physiological properties of interest, such as heart rate, temperature, SpO2, blood pressure, etc., therefore, the data related to the physiological properties could be presented on the machine case for patients or clinicians monitoring. Thereby, the machine case must mate with the cradle stably so as to electrically connect with the cables reliably.

A machine case with improved terminal module is designed to solve the aforementioned proposal.

SUMMARY OF THE INVENTION

According to one aspect of the present invention, a machine case comprises a sink-like main portion and opposite deck stations by two ends of said main portion in a longitudinal direction, and a terminal module. Said terminal module includes an insulator defining opposite top and bottom surfaces thereon in a vertical direction perpendicular to said longitudinal direction; a plurality of contacts retained to the insulator via a first insert molding process and arranged along a transverse direction perpendicular to both said longitudinal direction and said vertical direction. Each of said contacts is stamped and bent from sheet metal and unitarily formed with an upper contacting section exposed upon the top surface, and a lower contacting section exposed upon the bottom surface. Each of said upper contacting section and said lower contacting section extends along said longitudinal direction. Each of the upper contacting section and the lower contacting section is planar and stationary. One of said upper contacting section and said lower contacting section defines an exposed end for originally linking to a contact carrier. The insulator forms a plurality of recesses originally formed between the contacting sections of neighboring contacts in at least one of the top and bottom surfaces during the first insert molding while successively filled with material by the corresponding deck station in which said terminal module is embedded.

According to another aspect of the present invention, a machine case comprises a sink-like main portion and opposite deck stations by two ends of said main portion in a longitudinal direction, and a terminal module. Said terminal module includes an insulator defining opposite top and bottom surfaces thereon in a vertical direction perpendicular to said longitudinal direction; and a plurality of contacts retained to the insulator via a first insert molding process and arranged along a transverse direction perpendicular to both said longitudinal direction and said vertical direction. Each of said contacts is stamped and bent from sheet metal and unitarily formed with an upper contacting section exposed upon the top surface, and a lower contacting sections exposed upon the bottom surface, each of said upper contacting section and said lower contacting section extending along said longitudinal direction. Each of the upper contacting section and the lower contacting section is planar and stationary. One of said upper contacting section and said lower contacting section defines an exposed end for originally linking to a contact carrier. The main portion forms a receiving cavity with another terminal module located at an inner end and a pivotal door at an outer end in said longitudinal direction for receiving a battery pack.

Other objects, advantages and novel features of the invention will become more apparent from the following detailed description when taken in conjunction with the accompanying drawings.

DETAILED DESCRIPTION OF THE PREFERRED EMBODIMENT

Figure 1:
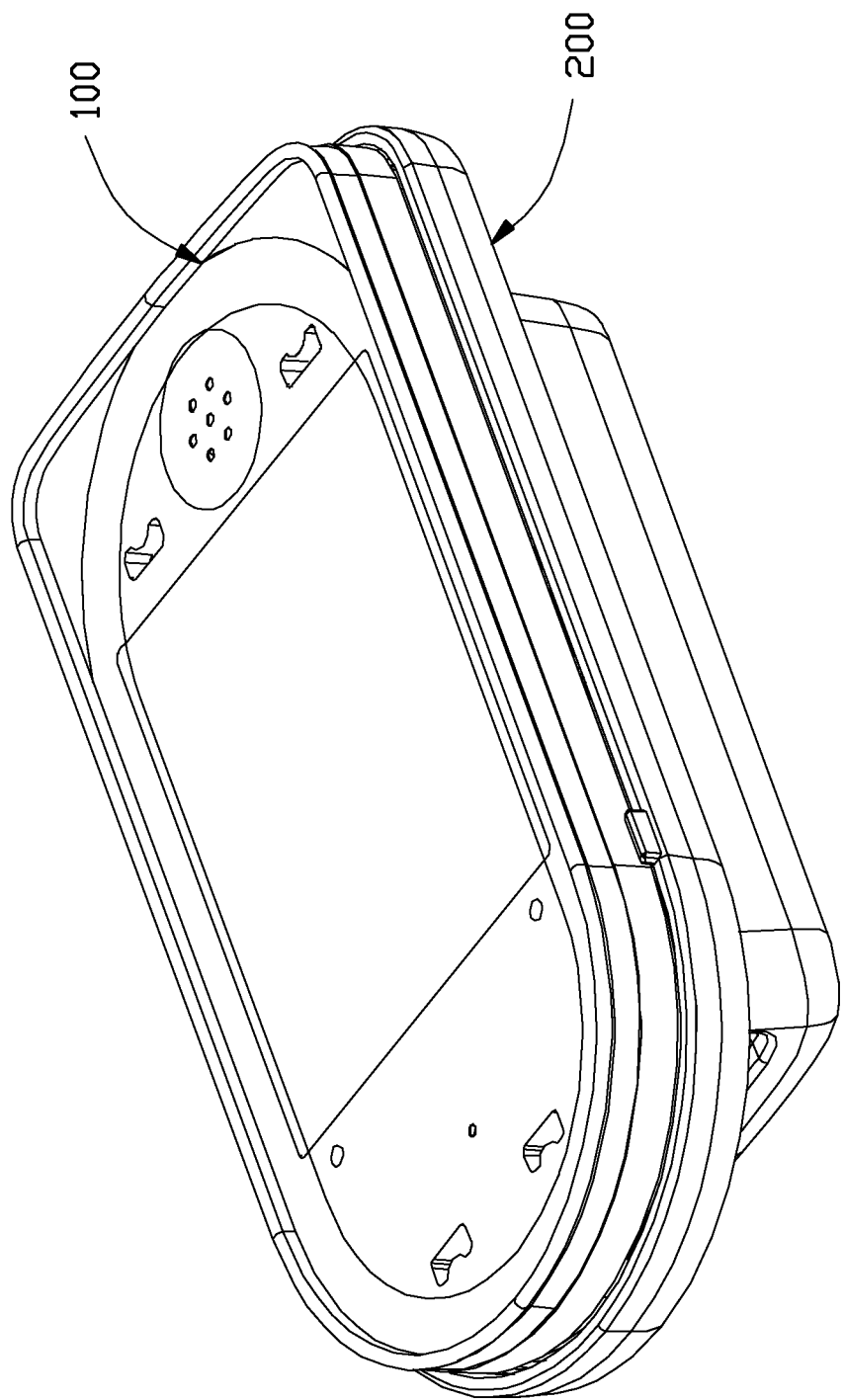
FIG. 1 is a downward assembled perspective view of the machine case with the corresponding electronic component therein, according to one embodiment of the invention.
Figure 2:
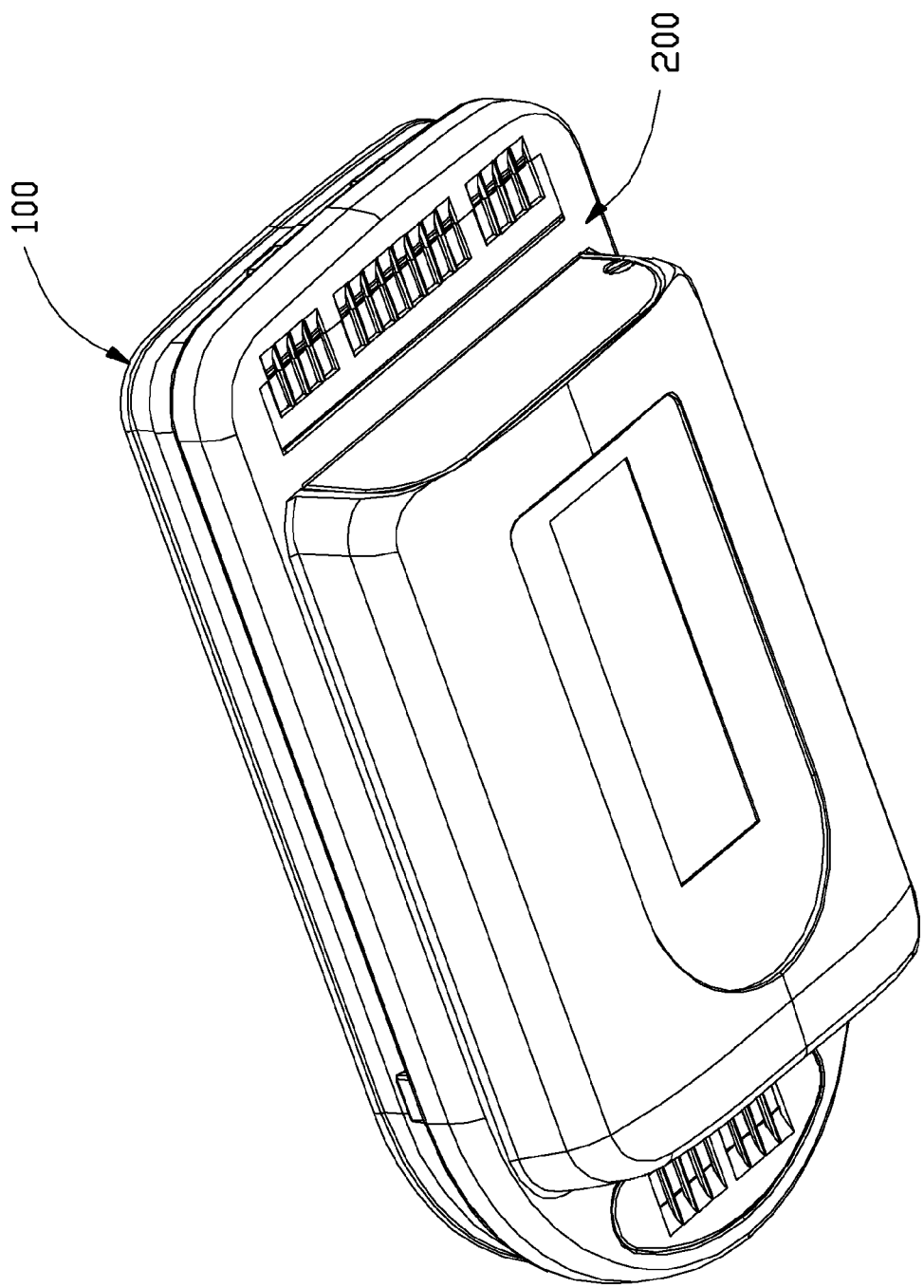
FIG. 2 is an upward assembled perspective view of the machine case with the corresponding electronic component therein of FIG. 1.
Figure 3:
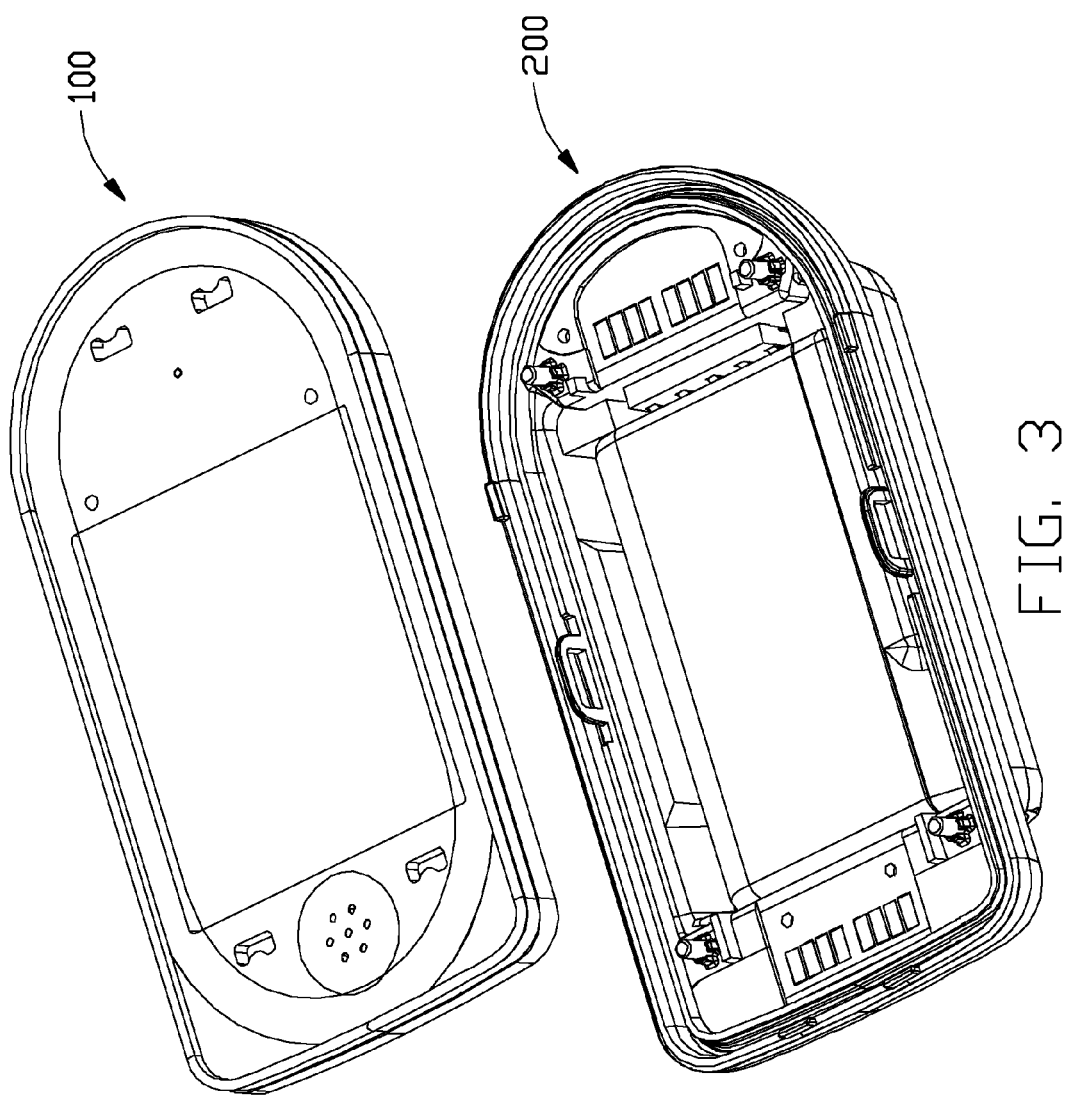
FIG. 3 is a downward exploded perspective view of the machine case with the corresponding electrical component removed therefrom of FIG. 1.
Figure 4:
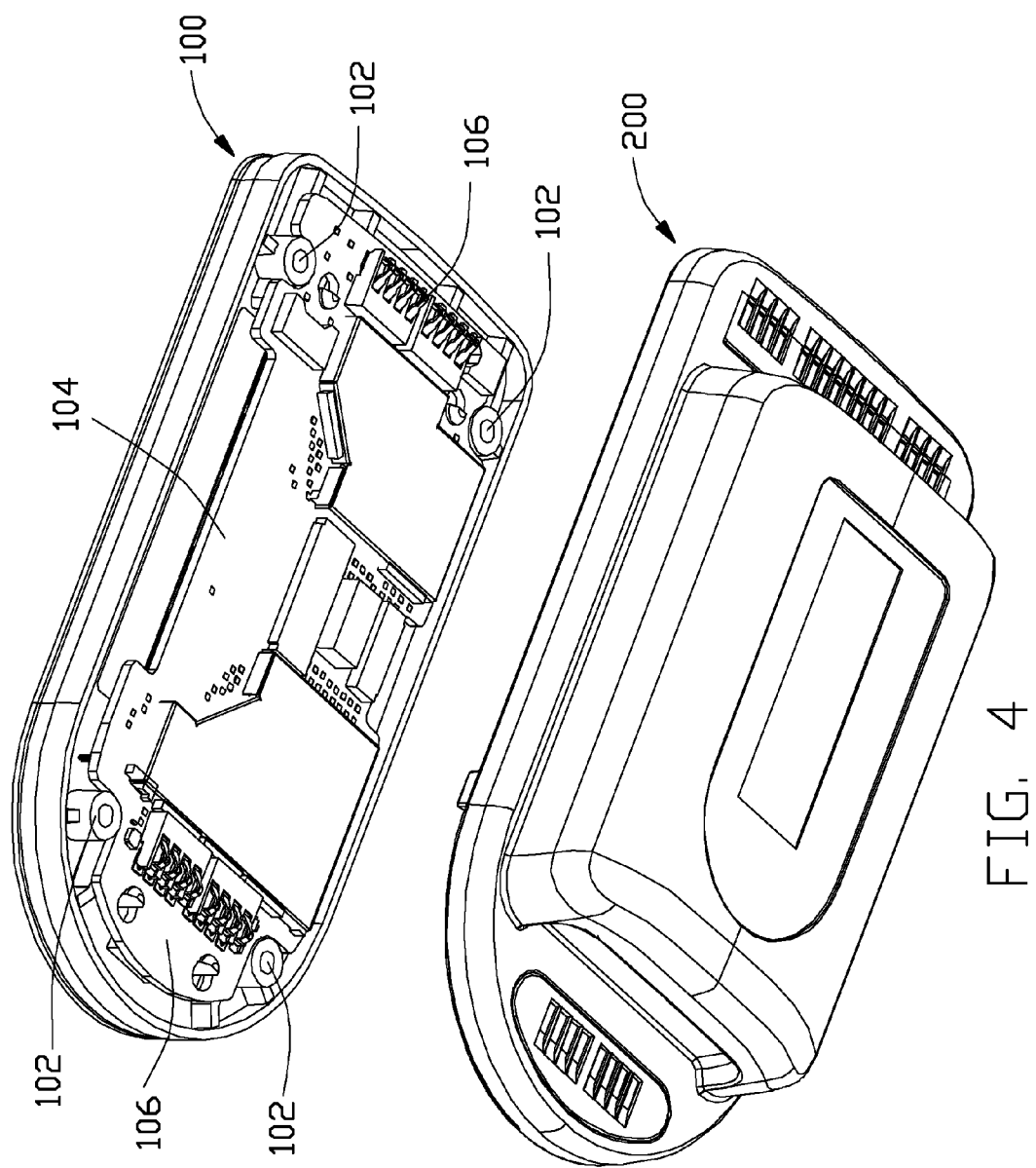
FIG. 4 is an upward exploded perspective view of the machine case with the corresponding electrical component removed therefrom of FIG. 3.
Figure 5:
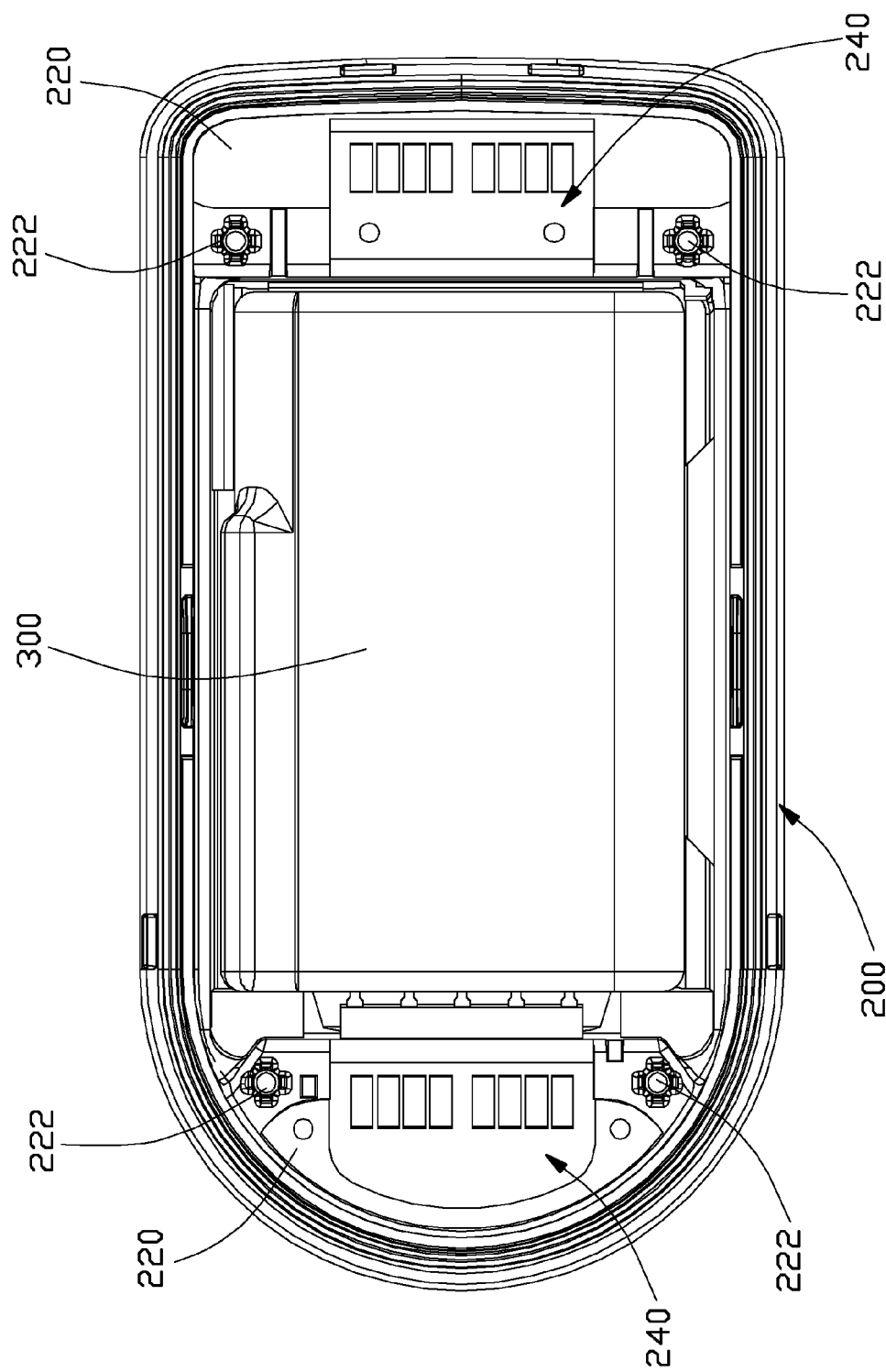
FIG. 5 is a top view of the machine case with the machine case without the corresponding electronic component therein of FIG. 1.
Figure 6:
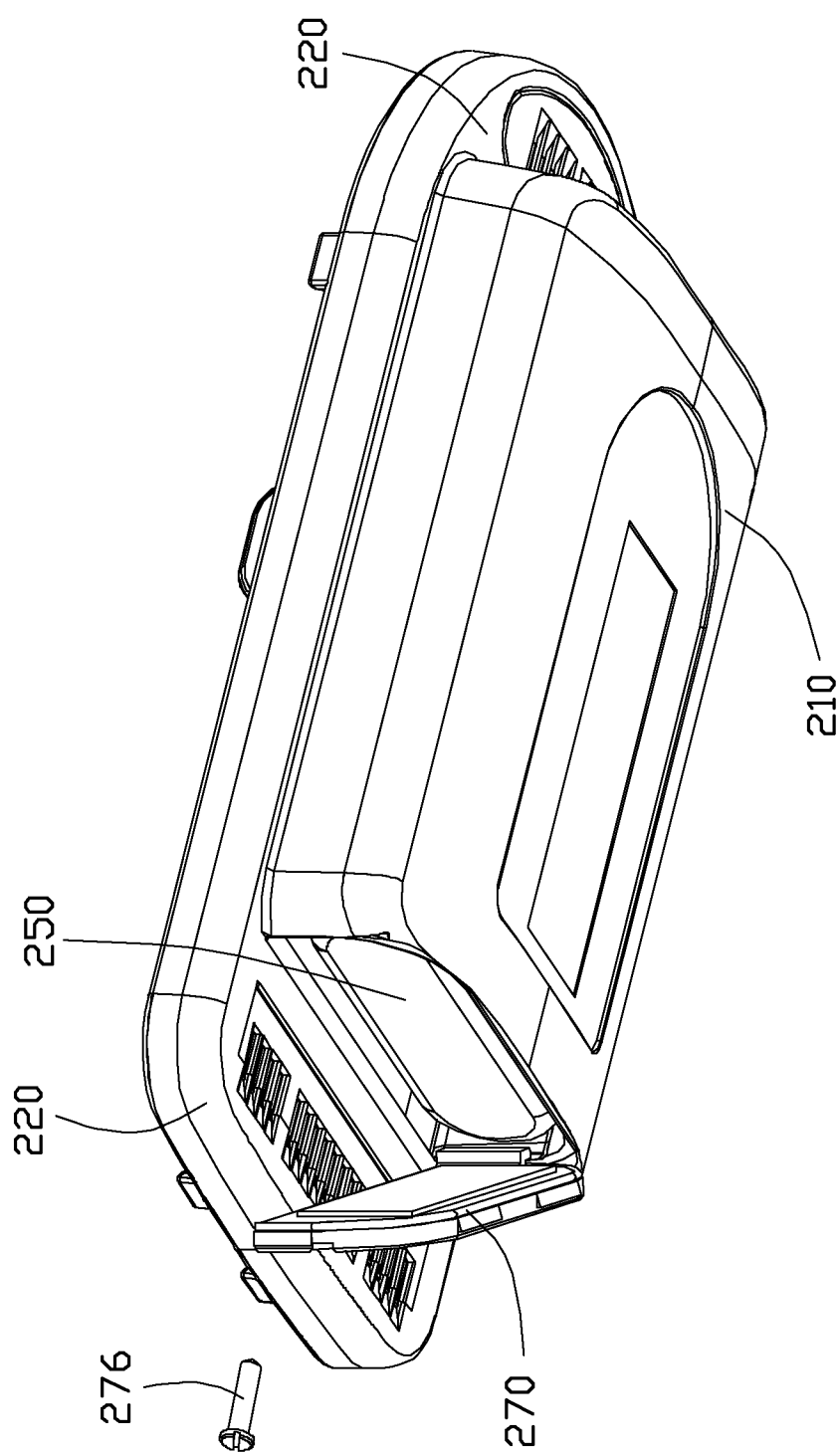
FIG. 6 is an upward partially exploded perspective view of the machine case with a replaceable battery pack therein of FIG. 1
Figure 7:
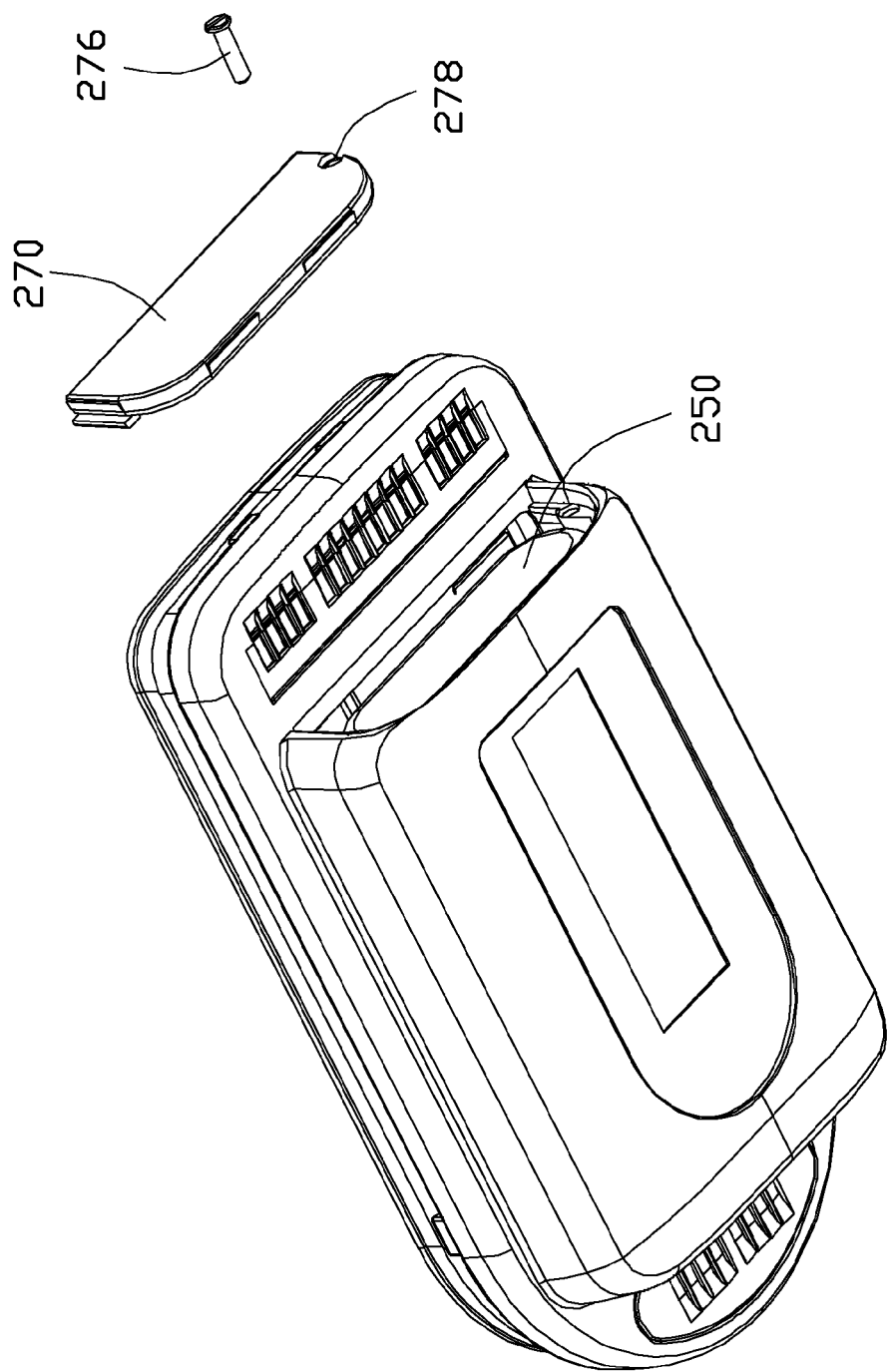
FIG. 7 is another upward partially exploded perspective view of the machine case with the replaceable battery pack therein of FIG. 1
Figure 8:
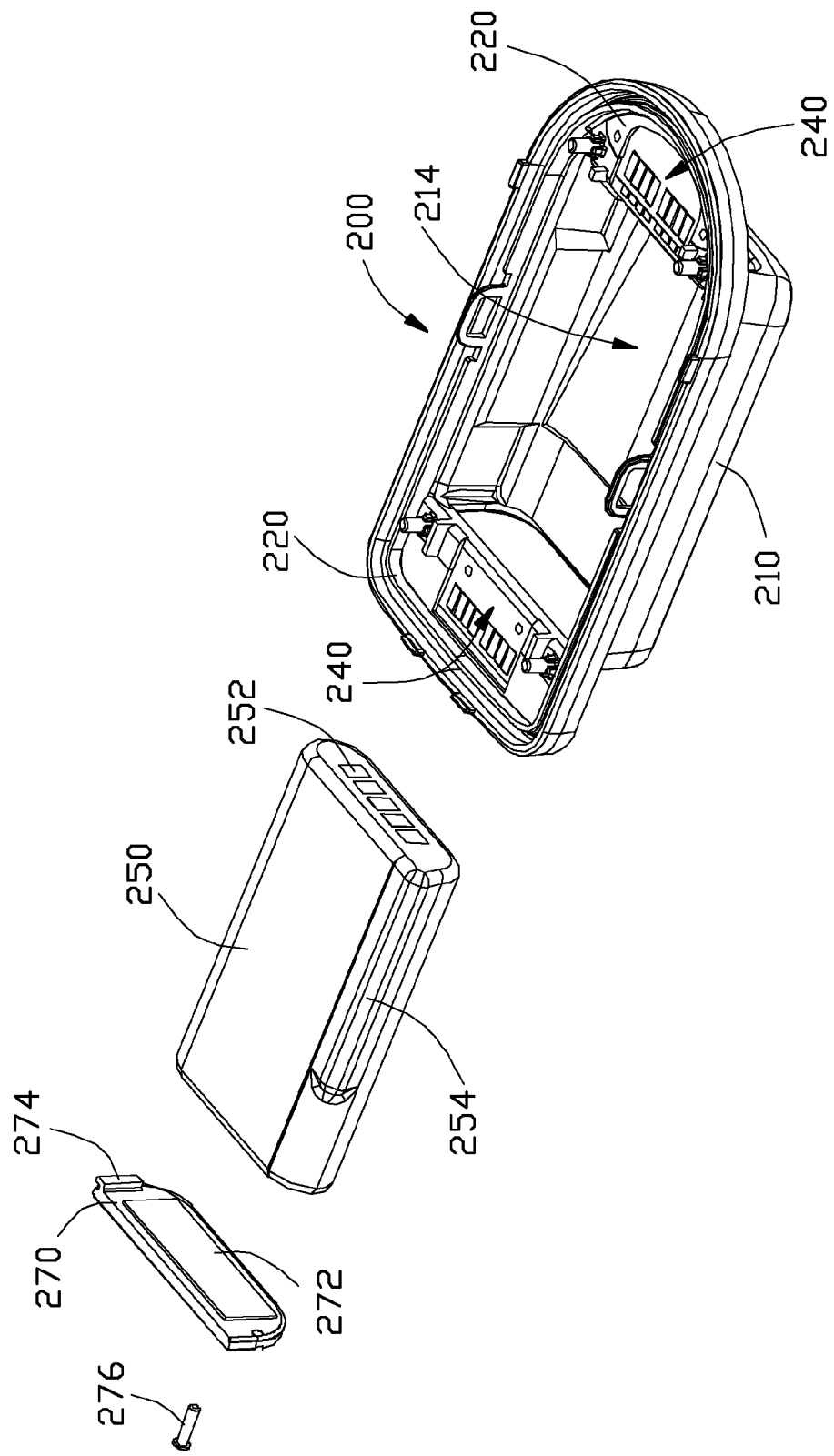
FIG. 8 is a downward exploded perspective view of the machine case with the replaceable battery pack removed therefrom of FIG. 1.
Figure 9:
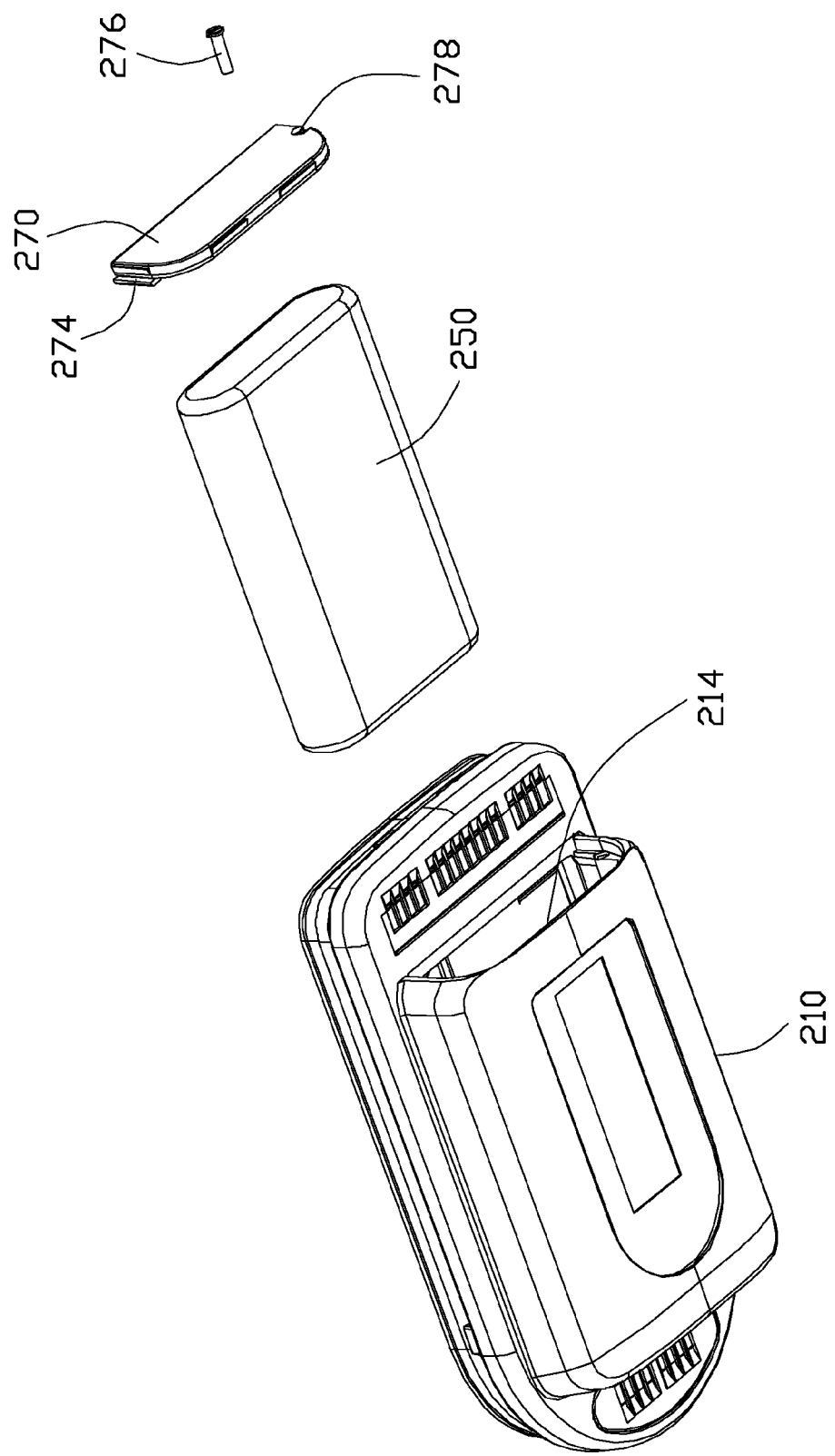
FIG. 9 is an upward exploded perspective view of the machine case with the replaceable battery pack removed therefrom of FIG. 1.
Figure 10:
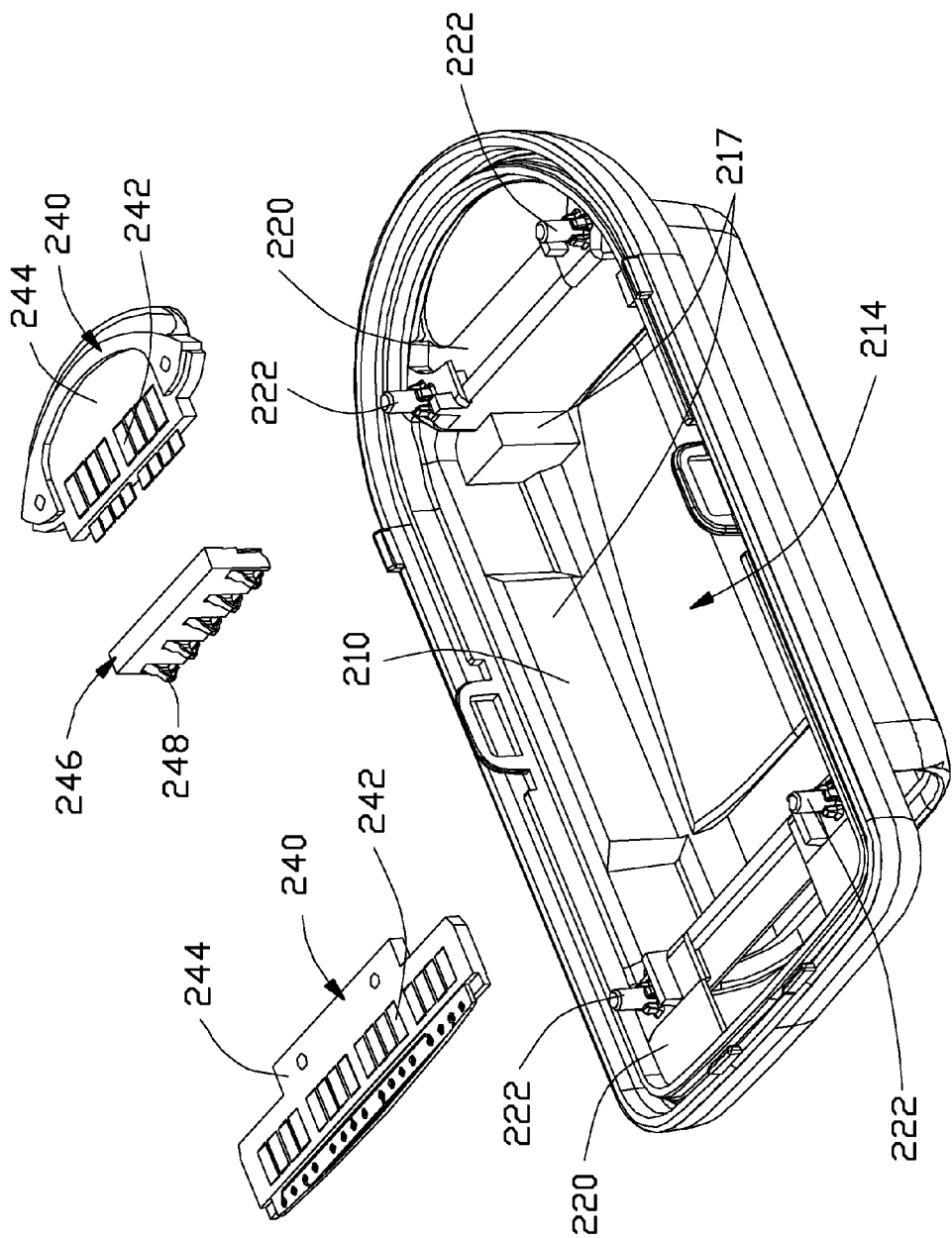
FIG. 10 is a downward exploded perspective view of the machine case with the corresponding terminal modules removed away therefrom of FIG. 1.
Figure 11:
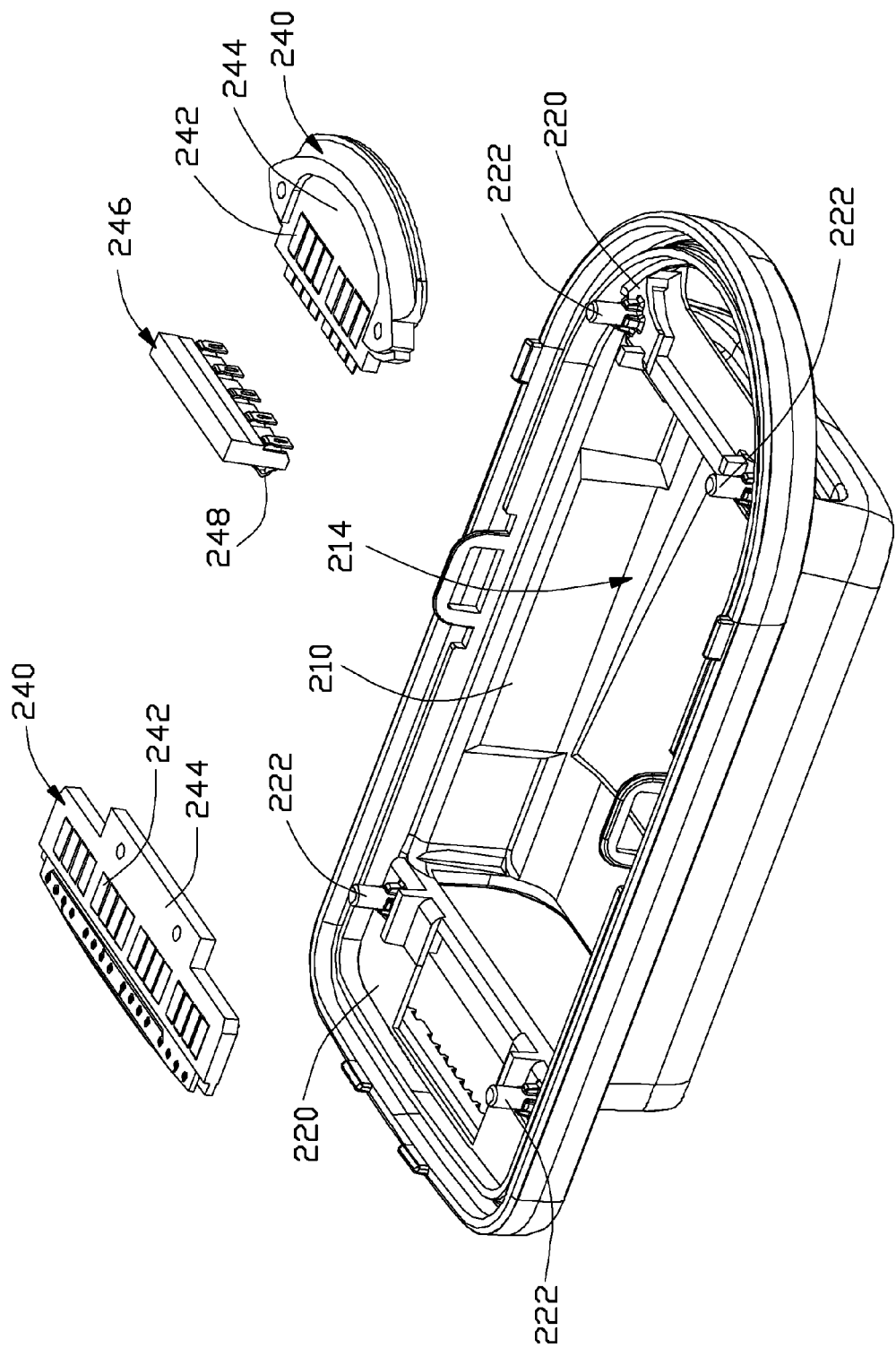
FIG. 11 is another downward exploded perspective view of the machine case with the corresponding terminal modules removed away therefrom of FIG. 1.
Figure 12:
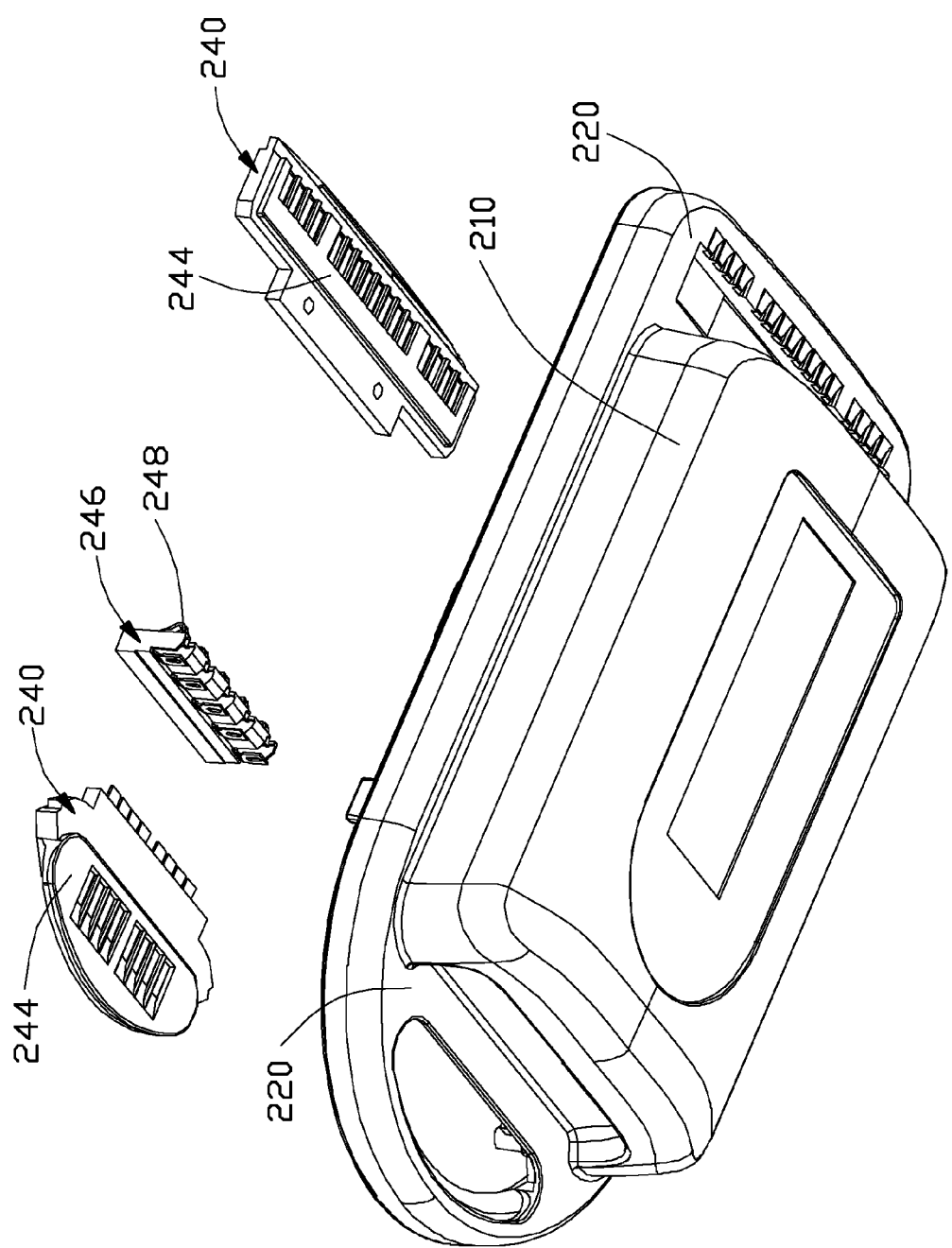
FIG. 12 is an upward exploded perspective view of the machine case with the corresponding terminal modules removed away therefrom of FIG. 1.
Figure 13:
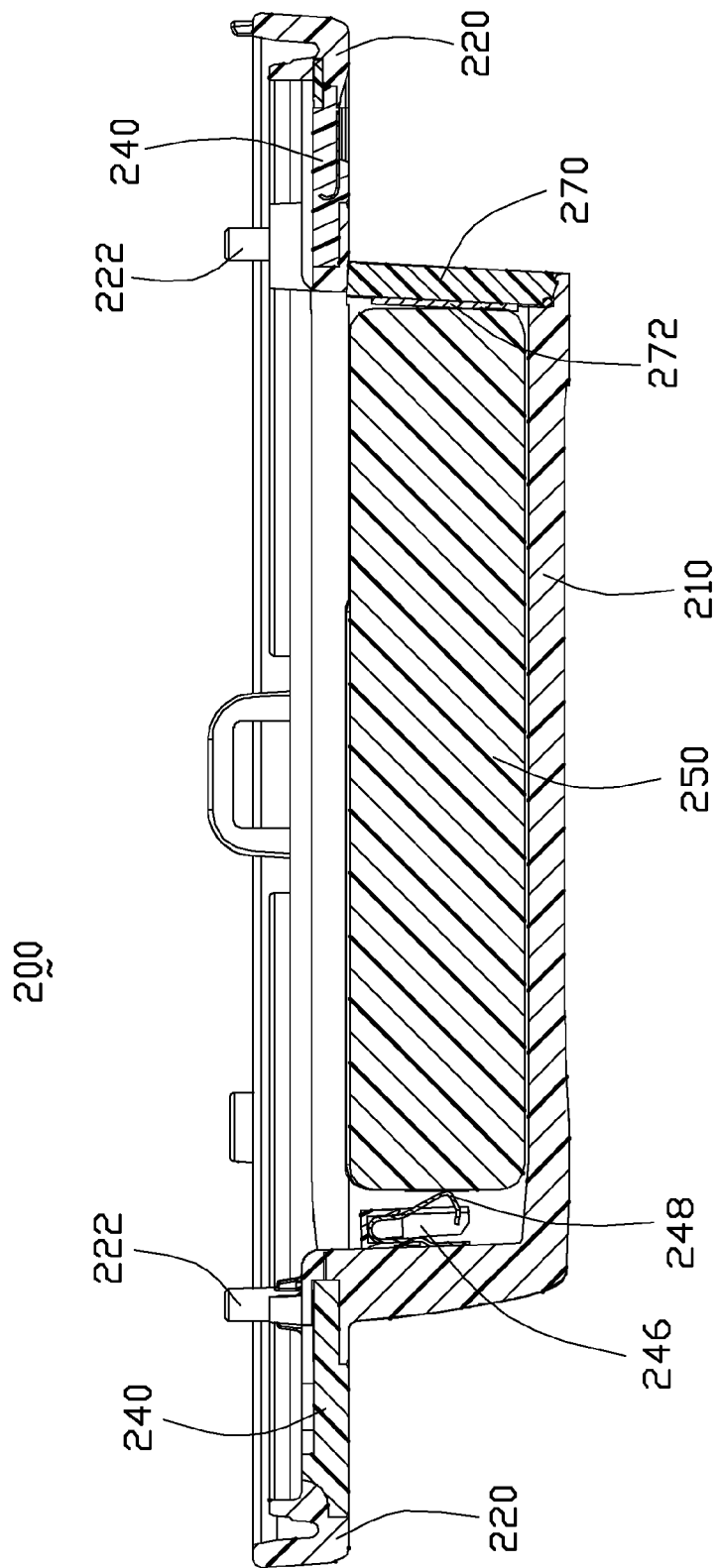
FIG. 13 is a cross-sectional view of the machines case with the replaceable battery pack therein of FIG. 1.
Figure 14:
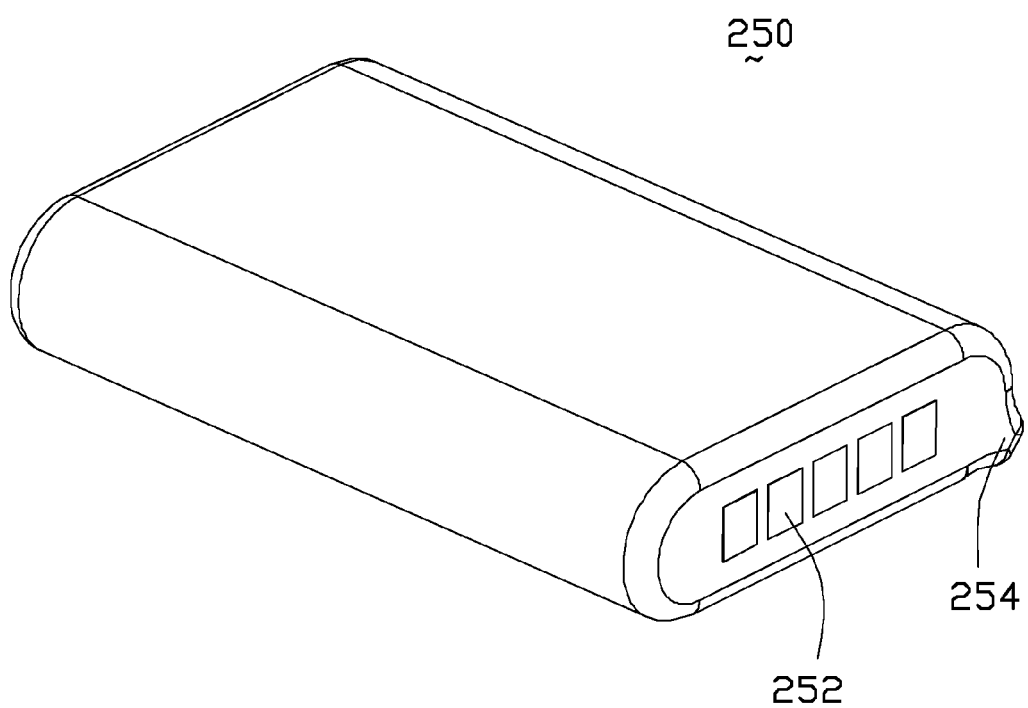
FIG. 14 is the replaceable battery pack used within the machine case of FIG. 1.
Figure 15:
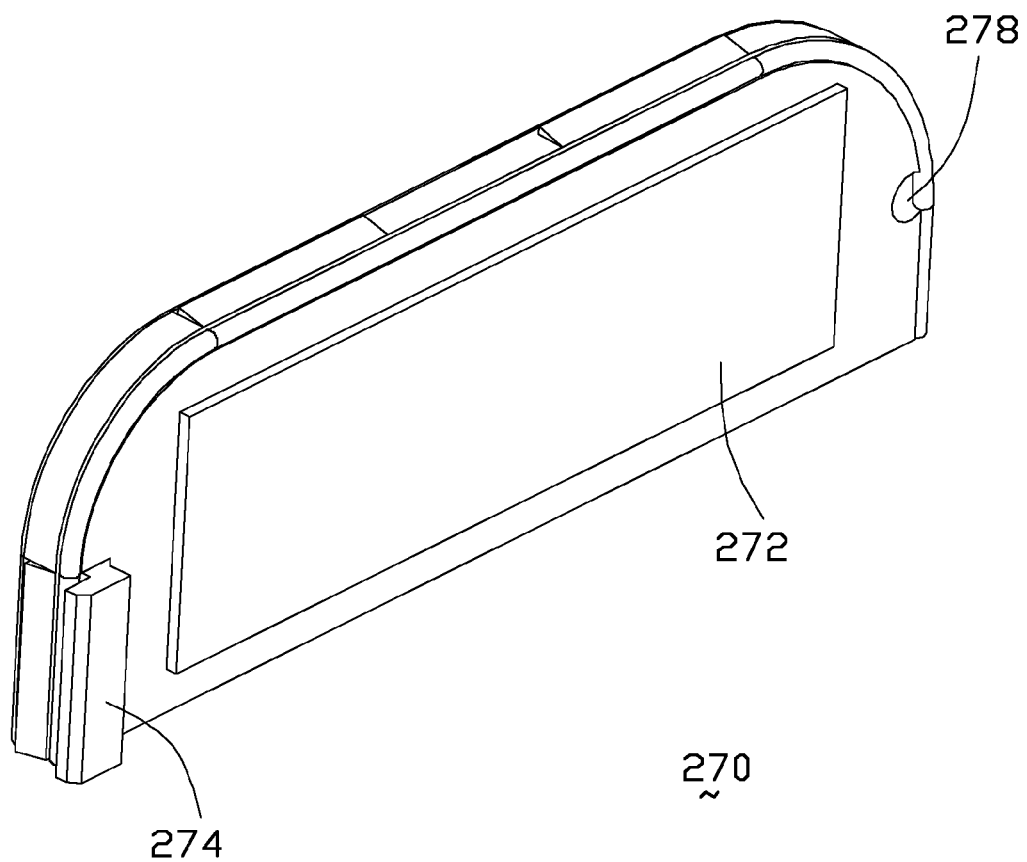
FIG. 15 is a perspective view of the pivotal door of the machine case of FIG. 1.

Reference will now be made in detail to the preferred embodiment of the present invention. Referring to FIGS. 1-15, a machine case 200 and an electronic component 100 loaded therein. The machine case 200 includes a sink type main body 210 with a pair of deck stations 220 by two sides in the lengthwise direction. A pair of terminal modules 240 are insert-molded within the corresponding deck stations 220, respectively, via forming an insert-molding process forming the main body 210 and the pair of deck stations 220, as illustrated in the second embodiment later. Notably, each terminal module 240 includes a plurality of contacts 242 embedded within an insulator 244 via an insert-molding process. A plurality of posts 222 upward extend from the deck station 220 into the corresponding through holes 102 of the electronic component 100. The electronic component 100 further includes a printed circuit board 104 with a pair of electrical connectors 106 thereon with the corresponding deflectable contacts for electrically and mechanically connecting to the pair of terminal modules 240.

The main body 210 forms an upward receiving cavity 214 to receive a replaceable battery pack 250 therein. The battery pack 250 includes a plurality of conductive pads 252 at an inner end. An additional terminal module 246 equipped with a plurality of contacts 248 retained by an insulator, is located at an inner end of the receiving cavity 214 for electrically and mechanically connecting to the conductive pads 252 of the battery pack 252. A moveable door 270 is pivotally mounted to an outer end of the receiving cavity 214. The door 270 includes an inner rubber pad 272 for absorbing an impact so as to assure the reliable connection between the conductive pads 252 and the contact 248. A hook structure 274 is formed at one lateral end of the door 270 to cooperate with the main body 210 to function as a pivot for allowing the door 270 to be rotated thereabouts to expose the receiving cavity 214 for loading/unloading the battery pack 270. A removable screw 276 extends into a locking hole 278 at the other lateral end of the door 270 for locking.

Understandably, the terminal module 246 may be electrically connected to the neighboring terminal module 240 via a transition device (not shown) for activating the whole assembly. In this embodiment, the main body 210 further forms positioning/protruding structures 217 for restraining the horizontal movement of the battery pack 250 in the receiving cavity 214. On the other hand, the interior of the main body 210 in the receiving cavity 214 may form the corresponding structure to comply with the protruding structure 254 for not only assuring one orientation of the battery pack 250 in the receiving cavity 214 but also preventing the upward movement of the battery pack 250 in the receiving cavity 214. Moreover, a sealing ring (not shown) may be optionally provided on a periphery of the door 270 for waterproofing.

Figure 16:
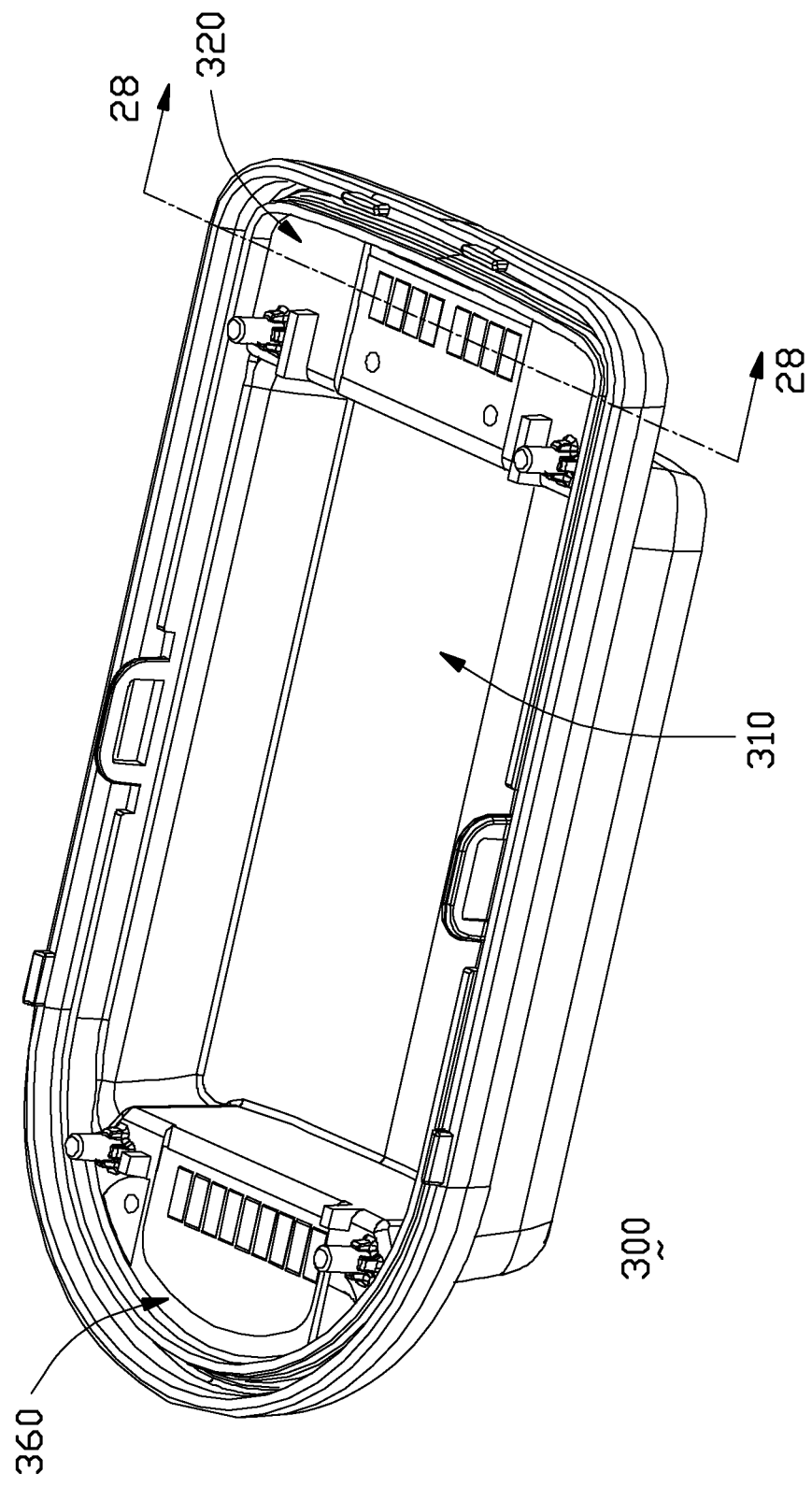
FIG. 16 is a downward perspective view of the machine case of another embodiment of the instant invention.
Figure 17:
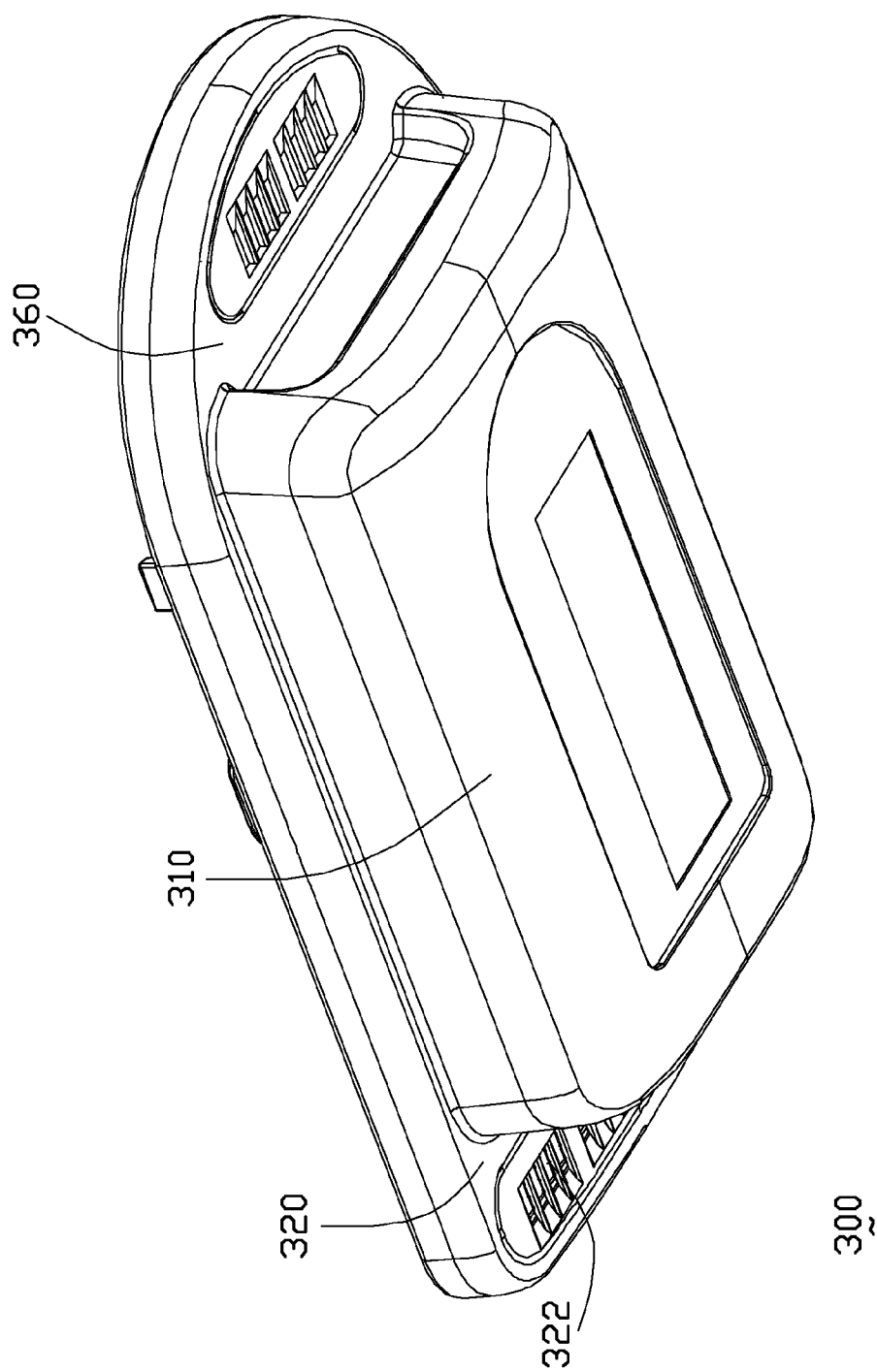
FIG. 17 is n upward perspective view of the machine case of FIG. 16.
Figure 18:
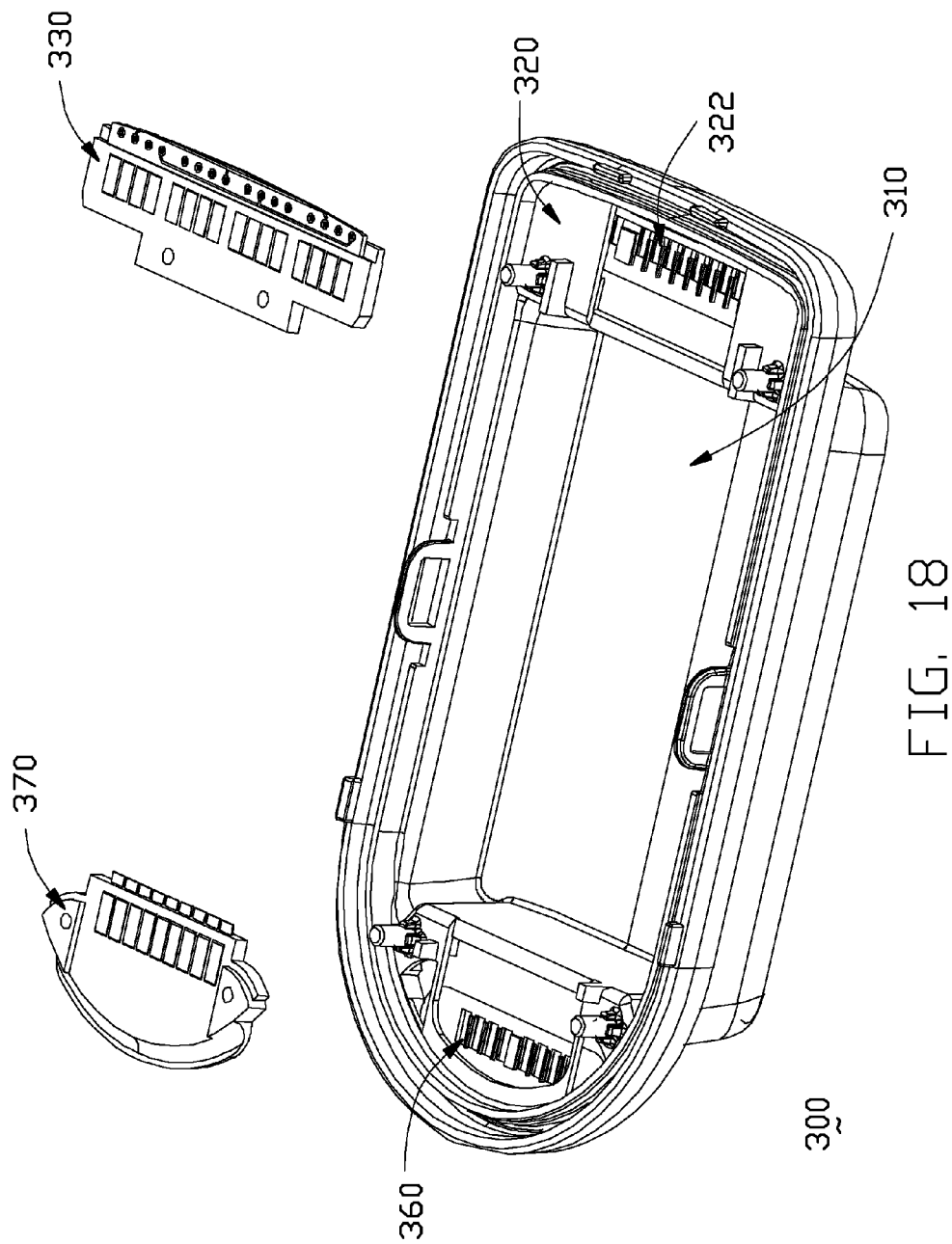
FIG. 18 is a downward exploded perspective view of the machine case of FIG. 16.
Figure 19:
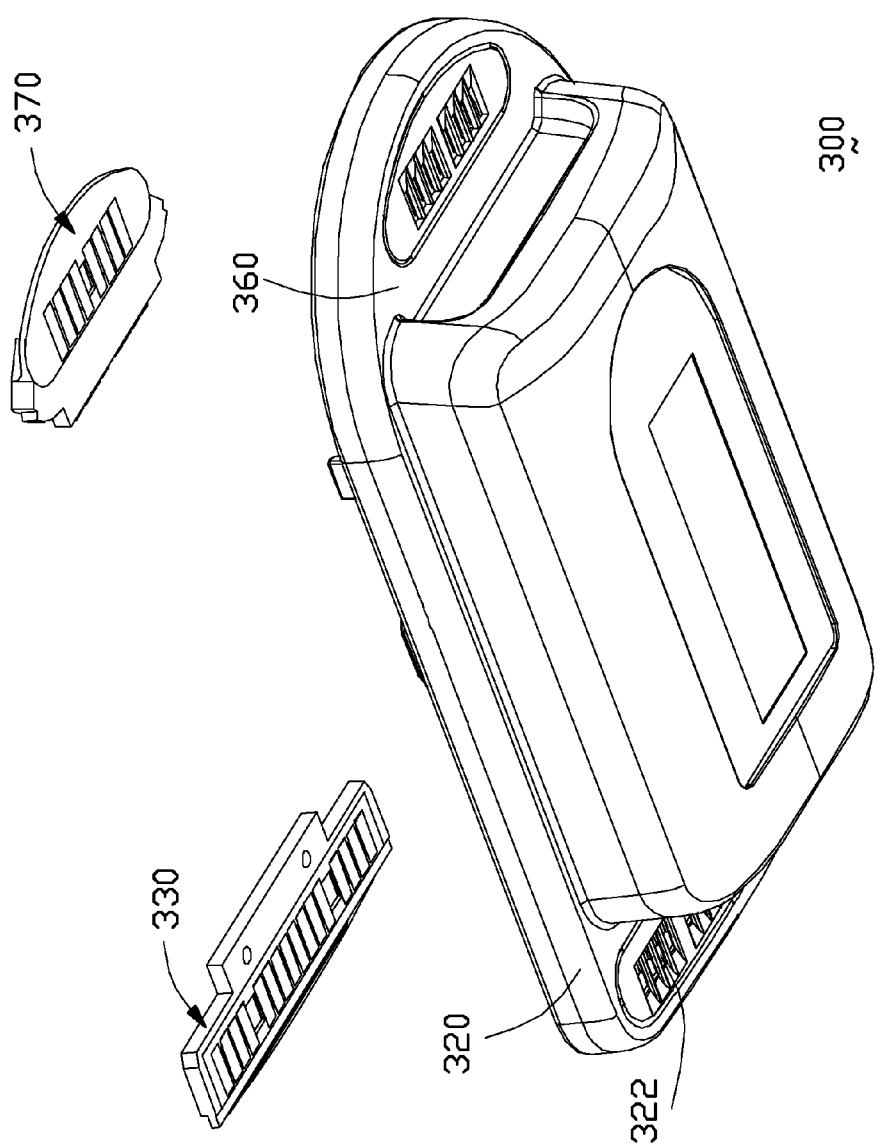
FIG. 19 is an upward exploded perspective view of the machine case of FIG. 16.
Figure 20:
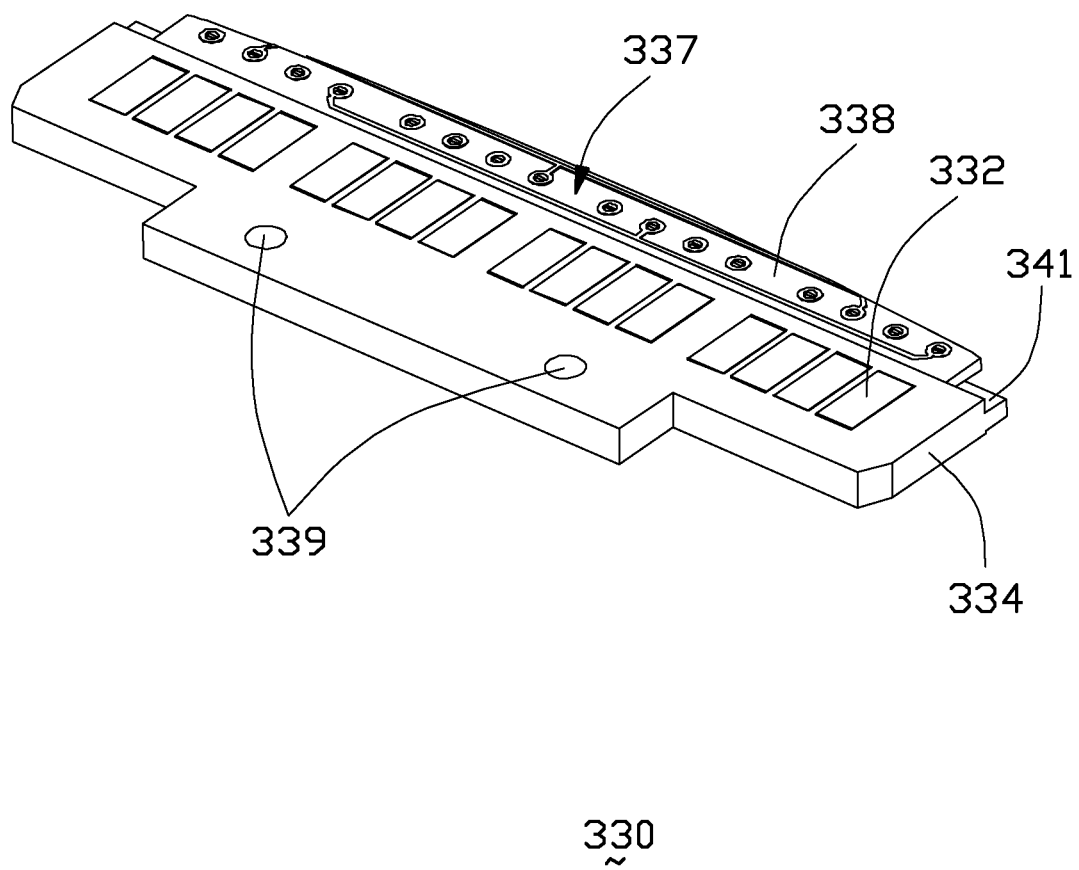
FIG. 20 is a downward perspective view of the first terminal module of the machines case of FIG. 16.
Figure 21:
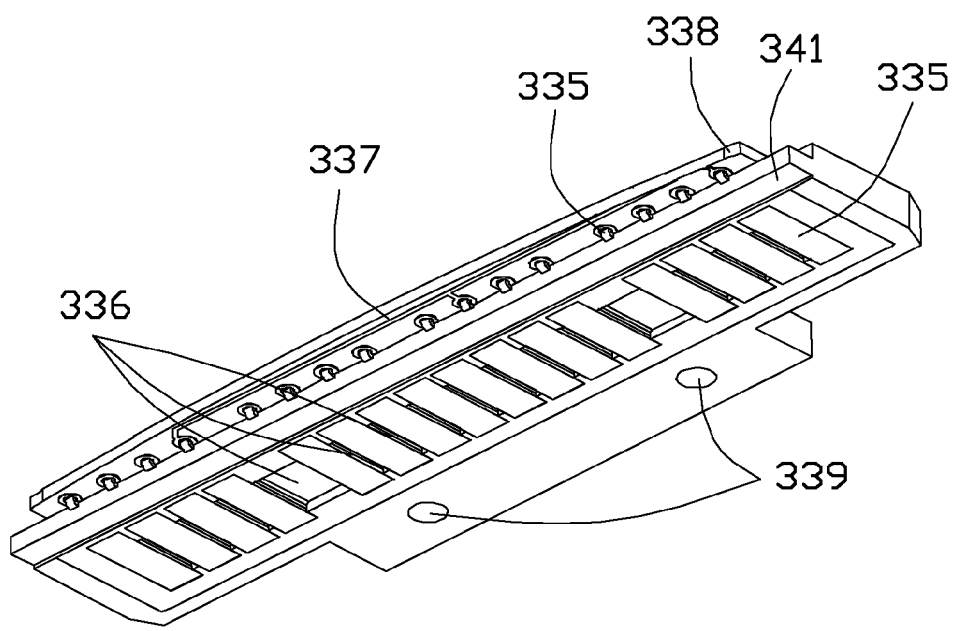
FIG. 21 is an upward perspective view of the first terminal module of machine case of FIG. 16.
Figure 22:
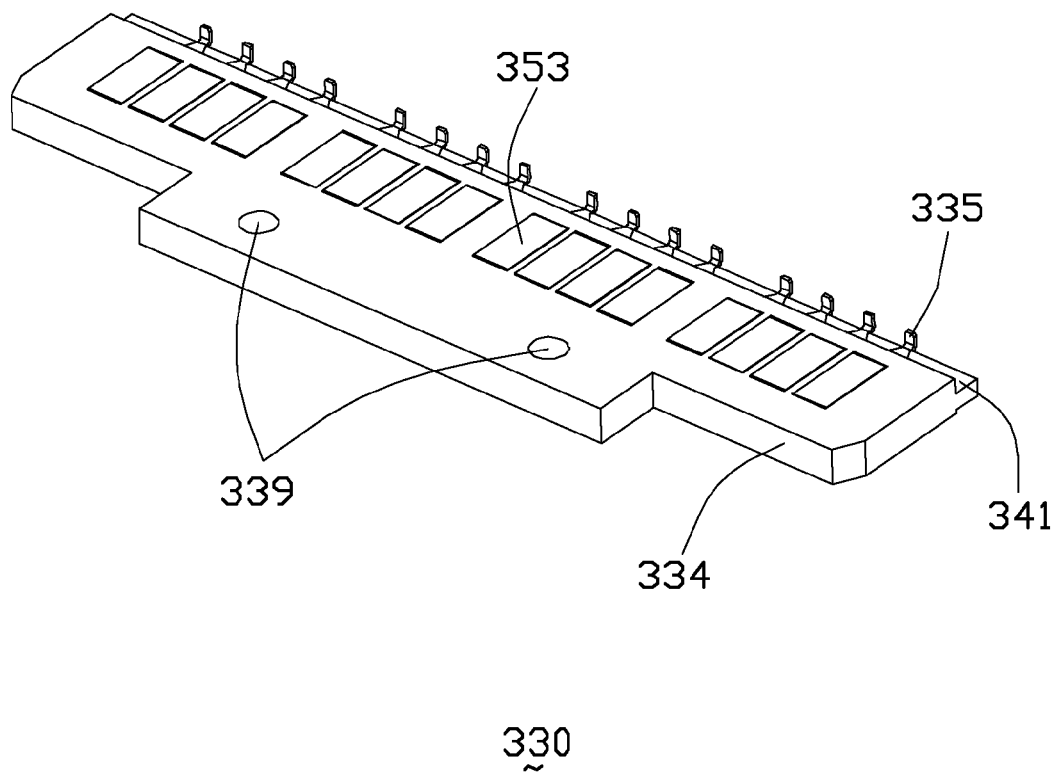
FIG. 22 is a downward perspective view of the first terminal module with the transitional printed circuit board removed therefrom, of the machine case of FIG. 16.
Figure 23:
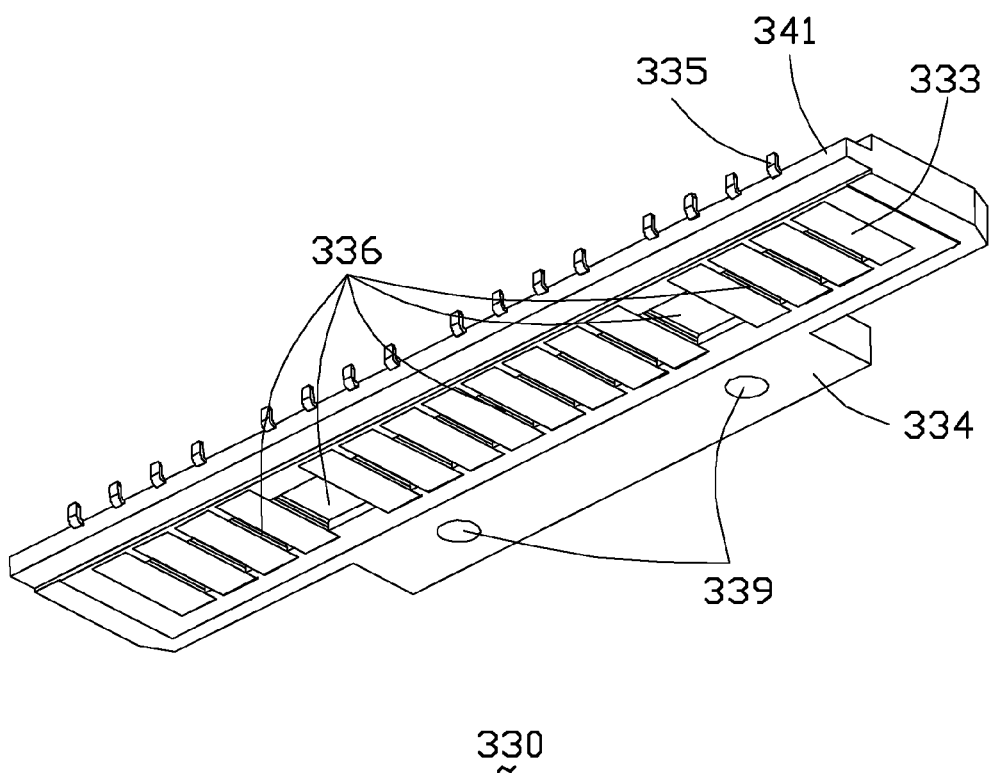
FIG. 23 is an upward perspective view of the first terminal module with the transitional printed circuit board removed therefrom, of the machine case of FIG. 16.
Figure 24:
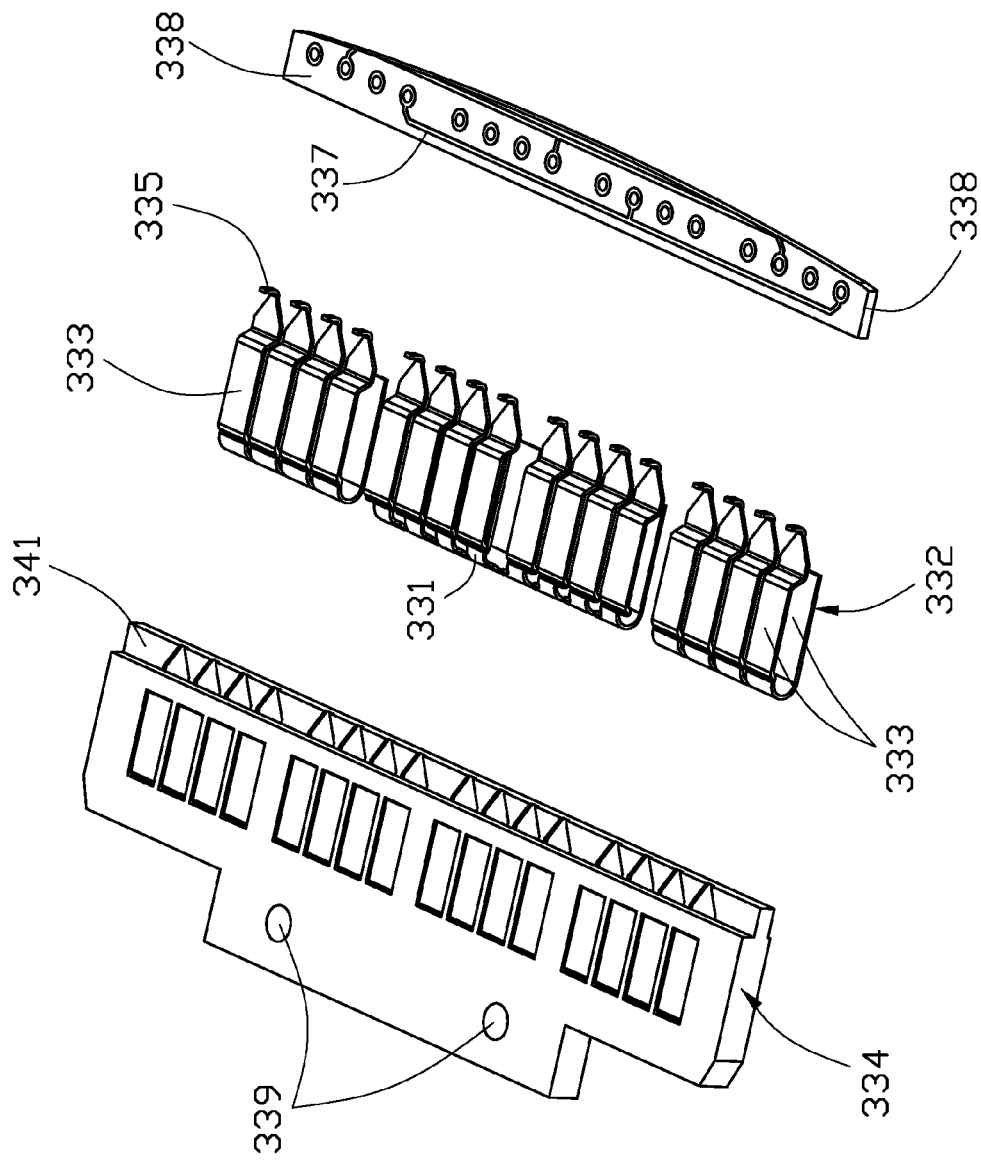
FIG. 24 is a downward exploded perspective view of the first terminal module of the machine case of FIG. 16.
Figure 25:
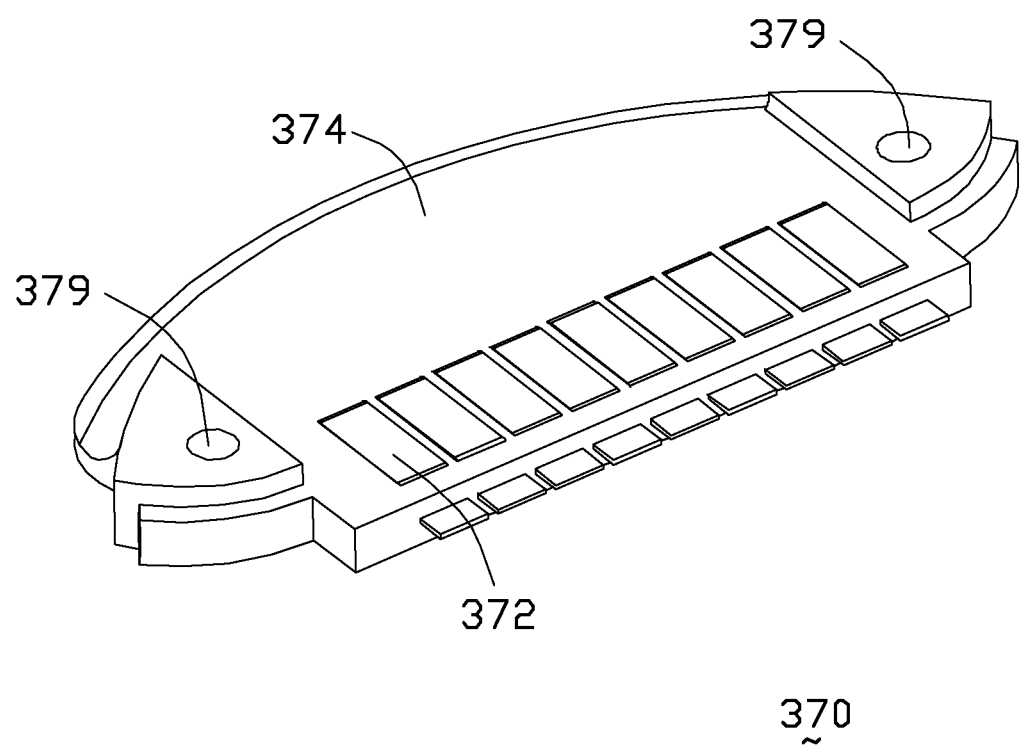
FIG. 25 is a downward perspective view of the second terminal module of the machine case of FIG. 16.
Figure 26:
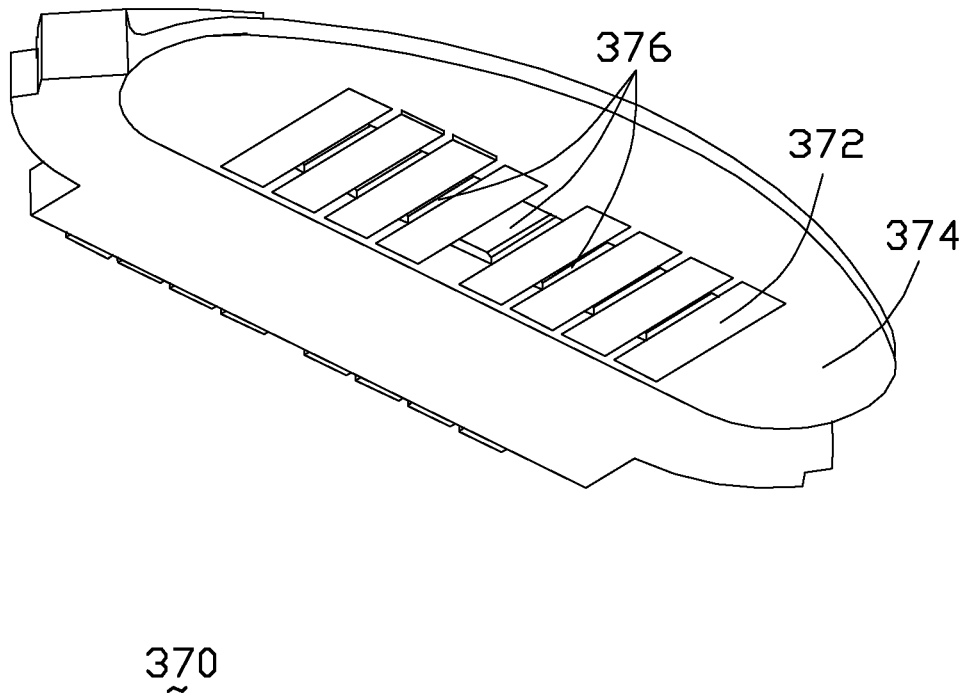
FIG. 26 is an upward perspective view of the second terminal module of the machine case of FIG. 16.
Figure 27:
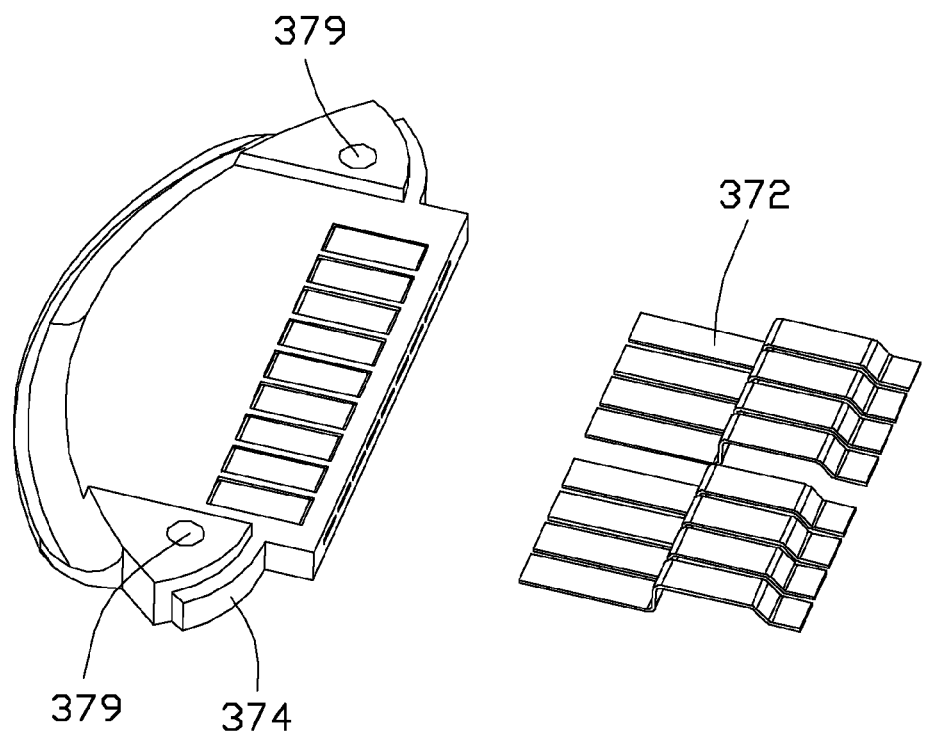
FIG. 27 is a downward perspective view of the second terminal module of the machine case of FIG. 16.
Figure 28:
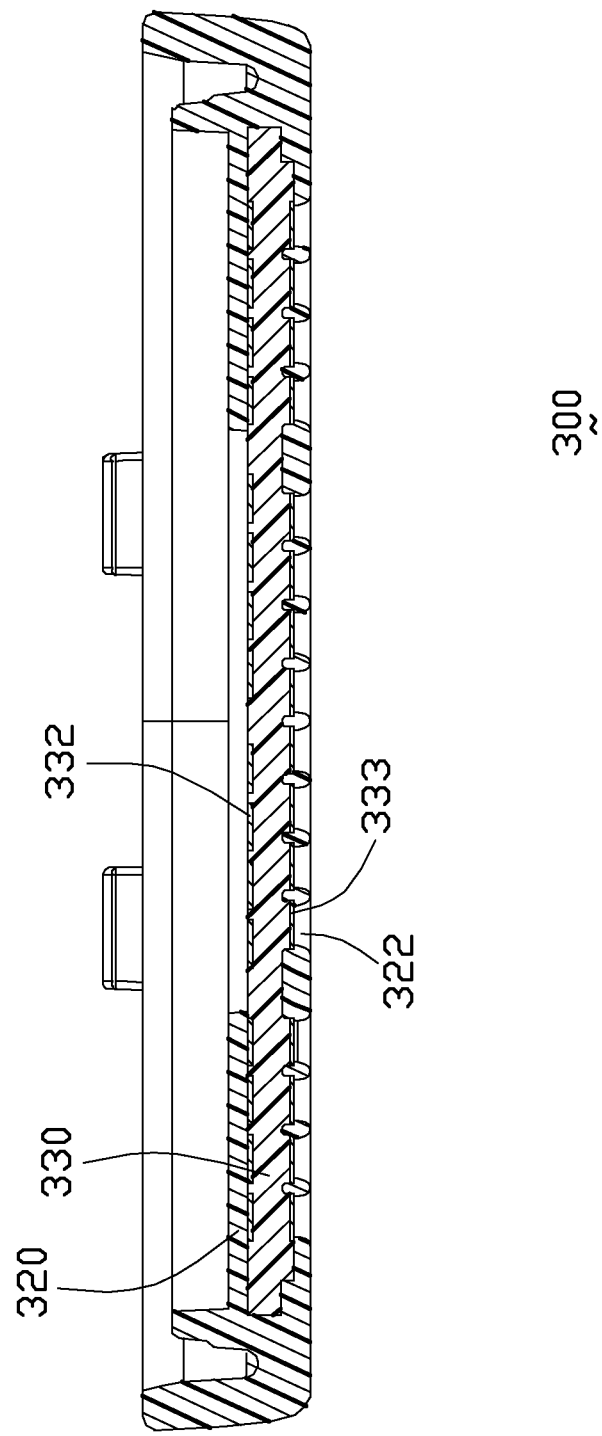
FIG. 28 is a cross-sectional view of the machine case of FIG. 16 to show the terminal module is embedded within the corresponding deck station.

Referring to FIGS. 16-28, a machine case 300 includes a sink-like main portion 310 with opposite first deck station 320 and second deck station 360 on two opposite ends in a longitudinal direction. A first terminal module 330 is insert-molded within the first deck station 320, and a second terminal module 370 is insert-molded within the second deck station 360. Compared with the embodiments disclosed in the previous provisional applications, the feature of this embodiment is to have the corresponding terminal modules embedded within the corresponding deck stations via the molding process forming the main portion and the deck stations, rather than mounting thereon after the deck stations have been formed by the corresponding molding process. Therefore, this embodiment uses the method of the so-called two shots or two insert-moldings to have the terminal module of the first insert-molding reliably retained within the corresponding deck stations via the second insert-molding, compared with the embodiments disclosed in the previous provisional application using one insert molding to form the terminal module which is retained upon the corresponding deck station which has been formed via an injection molding.

Similar to the embodiments disclosed in the previous provisional applications, the first terminal module 330 includes a plurality of first contacts 332 embedded within the corresponding first insulator 334 via an insert molding process. Anyhow, different from the embodiments in the previous provisional applications, in the bottom surface of the insulator 334 the partitions or recesses 336 between every adjacent two first contacts 332 are emptied for allowing the core-pins of the mold to occupy during the first insert-molding process for assuring true positions of the corresponding contacts with regard to the first insulator 334. Notably, such recesses 336 are filled with the material of the deck station 320 via the second insert-molding process during forming the main portion 310 and the first deck station 320 and the second deck station 360. Understandably, in this embodiment the recesses 336 are shorter than the contacting sections 333 of the neighboring first contacts 332 in the longitudinal direction, anyhow, alternately are longer, if necessary. Also, the recesses 335 may be applied to the upper surface of the first insulator 334, in necessary.

Similar to the embodiments disclosed in the previous provisional applications, a transitional printed circuit board 338 is positioned upon the first insulator 334 and mechanically and electrically connected to tails 335 of the corresponding contacts 332 to selectively short some of them via corresponding traces 337. The transitional printed circuit board 338 is further secured by the first deck station 320 after the second insert molding process. A flange structure 341 is formed on the first insulator 334 to support the transitional printed circuit board 338. A pair of alignment holes 339 are formed in the first insulator 334 for holding the first terminal module 330 in position during the second insert-molding process in which the first deck station 320 is formed with the first terminal module 330 embedded therein. Notably, two lateral regions of the upper surface of the first terminal module 330 including the contacting sections 333 of the corresponding first contacts 332, are covered by the material of the first deck station 320 in the vertical direction. Anyhow, the contacting sections 333 of the first contacts 332 on the bottom surface of the first insulator 334 are still downwardly exposed to an exterior through the corresponding openings 322. Similar to what is disclosed in the embodiments of the provisional applications, in the first terminal module 330, the contacting sections 333 of the eight first contacts 332 in a center region on the upper surface are divided into two groups to be essentially offset away from each other while those on the bottom surface are still located in the original positions. Therefore, for each of those eight first contacts 332, the contacting section 333 on the upper surface and that on the bottom surface are not aligned with each other in the vertical direction but in an offset manner. Understandably, because these two groups are symmetrical with each other, only one stamping mold is required for manufacturing. Each of those eight first contacts 332 has a joint 331 linking the respective contacting sections 33 on the upper and bottom surfaces, said joint 331 is embedded with the insulator 334 and hidden from the exterior, said joint 331 is narrower than the contacting sections 33 on the upper and bottom surfaces in the transverse direction.

Similarly, the second terminal module 370 includes a plurality of second contacts 372 embedded within the second insulator 374. The second insulator 374 forms a plurality of recesses 376 formed between the neighboring contacts 372 for positioning of the core-pins of the mold during the first insert-molding and successively filled with the material of the second deck station 360 during successively insert-molding the second terminal module 370 with the second deck station 360. A pair of alignment holes 379 are formed within the second insulator 374 for holding the second terminal module 370 in position during the second insert-molding in which the second deck station 360 is formed with the second terminal module 370 embedded therein.

It should be noted that even though in the embodiment the machine case and the cradle are involved and disclosed, the instant invention is essentially and primarily related to the terminal module and the connection parts only, so other portions may be others' invention. For example, the contacts can be stamped from Stainless Steel or Phos. Bronze and/or be plated with such coatings as Titanium Nitride or Rhodium to reduce corrosion when being used in harsh conditions. It should be noted that the invention is essentially related to the terminal module only and other portions of the machine case and the cradle may be others' invention.

What is claimed is:
1. A machine case comprising:
   a sink-like main portion and opposite deck stations by two ends of said main portion in a longitudinal direction; and
   a terminal module including:
   an insulator defining opposite top and bottom surfaces thereon in a vertical direction perpendicular to said longitudinal direction;
   a plurality of contacts retained to the insulator via a first insert molding process and arranged along a transverse direction perpendicular to both said longitudinal direction and said vertical direction, each of said contacts stamped and bent from sheet metal and unitarily formed with an upper contacting section exposed upon the top surface, and a lower contacting section exposed upon the bottom surface, each of said upper contacting section and said lower contacting section extending along said longitudinal direction; wherein
   each of the upper contacting section and the lower contacting section is planar and stationary; wherein
   one of said upper contacting section and said lower contacting section defines an exposed end for originally linking to a contact carrier; wherein
   the insulator forms a plurality of recesses originally formed between the contacting sections of neighboring contacts in at least one of the top and bottom surfaces during the first insert molding while successively filled with material by the corresponding deck station in which said terminal module is embedded.

2. The machine case as claimed in claim 1, wherein said terminal module further includes a transitional printed circuit board linked to the contacts with trace to short some together.

3. The machine case as claimed in claim 2, wherein the insulator includes a flange to support the transitional printed circuit board, said flange and transitional printed circuit board locates between the top and bottom surfaces of said insulator in the vertical direction.

4. The machine case as claimed in claim 1, wherein the upper contacting section and the lower contacting section are at least partially aligned with each other in the vertical direction.

5. The machine case as claimed in claim 1, wherein the upper surface and the lower surface are parallel to each other horizontally.

6. The machine case as claimed in claim 1, wherein the contact is of a folded type with a joint linking the upper contacting section and the lower contacting section, and said joint is embedded with the insulator and hidden from the exterior.

7. The machine case as claimed in claim 6, wherein said joint is narrower than either the upper contacting section and the lower contacting section in the transverse direction.

8. The machine case as claimed in claim 1, wherein in some of said contacts, the upper contacting section and the lower contacting section are offset from each other in the transverse direction.

9. The machine case as claimed in claim 8, wherein said some of the contacts are divided into two opposite groups, and the upper contacting sections in one group are offset away from those in the other group in said transverse direction in a symmetrical manner with regard to a centerline between said two groups.

10. A machine case comprising:
    a sink-like main portion and opposite deck stations by two ends of said main portion in a longitudinal direction; and a terminal module including:
an insulator defining opposite top and bottom surfaces thereon in a vertical direction perpendicular to said longitudinal direction;
a plurality of contacts retained to the insulator via a first insert molding process and arranged along a transverse direction perpendicular to both said longitudinal direction and said vertical direction, each of said contacts stamped and bent from sheet metal and unitarily formed with an upper contacting section exposed upon the top surface, and a lower contacting sections exposed upon the bottom surface, each of said upper contacting section and said lower contacting section extending along said longitudinal direction; wherein
each of the upper contacting section and the lower contacting section is planar and stationary; wherein
one of said upper contacting section and said lower contacting section defines an exposed end for originally linking to a contact carrier; wherein
the main portion forms a receiving cavity with another terminal module located at an inner end and a pivotal door at an outer end in said longitudinal direction for receiving a battery pack.

11. The machine case as claimed in claim 10, wherein said receiving cavity sinks under the opposite deck stations in the vertical direction, said terminal module is disposed in a horizontal manner while said another terminal module is disposed in a vertical manner.

12. The machine case as claimed in claim 10, wherein said some of the contacts are divided into at least two opposite groups, each contact of said two groups is of a folded type with a joint linking the upper contacting section and the lower contacting section, and said joint is narrower than either the upper contacting section and the lower contacting section in the transverse direction; all of the lower contacting sections of said two groups are arranged at equal intervals in the transverse direction, and the upper contacting sections in one group are offset away from those in the other group in said transverse direction in a symmetrical manner with regard to a centerline between said two groups.

13. A machine case comprising:
an insulative base defining a sink-like main portion and at least one deck station at one end along a longitudinal direction;
a contact module disposed in said deck station and including an insulator with a plurality of contacts embedded therein via a first insert-molding process, each of said contacts including an upper contacting section and a lower contacting section spaced from and opposite to each other in a vertical direction perpendicular to said longitudinal direction;
the deck station being applied upon the contact module in a surrounding manner via a second insert-molding process; wherein
some of said upper contacting sections are hidden below a top surface of the deck station while remainders are exposed upwardly to an exterior, and the lower contacting sections are exposed downwardly to the exterior.

14. The machine case as claimed in claim 13, wherein a bottom surface of the deck station further forms a plurality of openings not only to expose the corresponding lower contacting sections but also to receive therein a corresponding mating terminal of a cradle located under the case machine.

15. The machine case as claimed in claim 13, further including a transitional printed circuit board mechanically connected to the contacts and selectively electrically shoring some of said contacts, wherein said transitional printed circuit board associated with the contact module, is embedded within the deck station via said second insert-molding process.

16. The machine case as claimed in claim 15, wherein each of said contacts includes a tail section extending into the vertical direction to be secured to the transitional printed circuit board.

17. The machine case as claimed in claim 13, wherein said contact module forms at least one alignment hole to cooperate with an external post to hold the contact module in position during the second insert-molding process to form the deck station thereon.

18. The machine case as claimed in claim 13, wherein said insulator forms a recess in the first insert-molding process while filled with material of the deck station during the second insert-molding process so as to be unitarily formed with the deck station for securing.

19. The machine case as claimed in claim 13, wherein the upper contacting section and the lower contacting section are different from each other in length along the longitudinal direction, and offset from each other in a transverse direction perpendicular to both said longitudinal direction and said vertical direction.

20. The machine case as claimed in claim 13, wherein said main portion receives therein a battery which is removable along the longitudinal direction via a movable door.

* * * * *